US012178536B2

(12) United States Patent
Overmyer et al.

(10) Patent No.: US 12,178,536 B2
(45) Date of Patent: Dec. 31, 2024

(54) DISABLING SURGICAL TOOLS DUE TO MANUAL BAILOUT

(71) Applicant: CILAG GMBH INTERNATIONAL, Zug (CH)

(72) Inventors: Mark D. Overmyer, Cincinnati, OH (US); Benjamin Lawrence Bertram, Crestview, KY (US); Christopher A. Denzinger, Cincinnati, OH (US); Robert Louis Koch, Jr., Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/506,000

(22) Filed: Nov. 9, 2023

(65) Prior Publication Data

US 2024/0065789 A1     Feb. 29, 2024

Related U.S. Application Data

(63) Continuation of application No. 17/563,530, filed on Dec. 28, 2021, now Pat. No. 11,813,032, which is a
(Continued)

(51) Int. Cl.
*A61B 17/072*        (2006.01)
*A61B 17/068*        (2006.01)
(Continued)

(52) U.S. Cl.
CPC .......... *A61B 34/37* (2016.02); *A61B 17/068* (2013.01); *A61B 17/072* (2013.01);
(Continued)

(58) Field of Classification Search
CPC .............. A61B 17/068; A61B 17/0686; A61B 17/072; A61B 17/07207; A61B 17/115;
(Continued)

(56) References Cited

U.S. PATENT DOCUMENTS 8,608,045 B2 * 12/2013 Smith ................ A61B 17/0686
                                                        227/181.1
9,072,535 B2 *  7/2015 Shelton, IV ..... A61B 17/07207
(Continued)

*Primary Examiner* — Scott A Smith
(74) *Attorney, Agent, or Firm* — Vorys, Sater, Seymour and Pease LLP

(57) ABSTRACT

A surgical tool includes a drive housing removably coupled to a tool driver of a robotic surgical system, a shaft extending from the drive housing, an end effector arranged at an end of the shaft, and a computer system. The computer system is programmed to send a command signal to a motor of the tool driver to drive rotation of a drive shaft mounted within the drive housing, monitor torque and rotational motion of the motor with a torque sensor and a rotary encoder, respectively, in communication with the computer system, measure an unexpected change in the torque or the rotational motion of the motor with the torque sensor or the rotary encoder when the surgical tool is manually bailed out by manually rotating the drive shaft and backdriving the motor, report the unexpected change as a bailout signal, and disable the surgical tool once the bailout signal is received.

20 Claims, 10 Drawing Sheets

Related U.S. Application Data continuation of application No. 16/427,818, filed on May 31, 2019, now Pat. No. 11,219,495.

(51) Int. Cl.
| | |
|---|---|
| *A61B 34/00* | (2016.01) |
| *A61B 34/37* | (2016.01) |
| *A61B 90/00* | (2016.01) |
| A61B 17/00 | (2006.01) |
| A61B 17/29 | (2006.01) |
| A61B 34/30 | (2016.01) |

(52) U.S. Cl.
CPC ........ *A61B 17/07207* (2013.01); *A61B 34/74* (2016.02); *A61B 90/361* (2016.02); *A61B 2017/00407* (2013.01); *A61B 2017/00477* (2013.01); *A61B 2017/07214* (2013.01); *A61B 2017/07285* (2013.01); *A61B 2017/2927* (2013.01); *A61B 2017/2943* (2013.01); *A61B 2034/305* (2016.02); *A61B 34/71* (2016.02); *A61B 2034/742* (2016.02); *A61B 2090/066* (2016.02); *A61B 2090/371* (2016.02)

(58) Field of Classification Search
CPC .......... A61B 2017/00017; A61B 2017/00477; A61B 2017/07214; A61B 2017/07228; A61B 2017/2927; A61B 2017/2943; A61B 34/30; A61B 34/37; A61B 34/71; A61B 34/74; A61B 90/361; A61B 90/98
USPC .............. 227/19, 175.1, 175.2, 176.1, 180.1; 606/1, 139, 219
See application file for complete search history.

(56) References Cited

U.S. PATENT DOCUMENTS

| | | | | |
|---|---|---|---|---|
| 9,332,987 | B2* | 5/2016 | Leimbach | ............ A61B 17/105 |
| 9,439,649 | B2* | 9/2016 | Shelton, IV | ............ A61B 17/00 |
| 9,629,623 | B2* | 4/2017 | Lytle, IV | ............ A61B 18/1445 |
| 9,629,629 | B2* | 4/2017 | Leimbach | ........ A61B 17/07207 |
| 11,219,495 | B2* | 1/2022 | Overmyer | ........ A61B 17/07207 |
| 11,813,032 | B2* | 11/2023 | Overmyer | ........ A61B 17/07207 |

* cited by examiner

DISABLING SURGICAL TOOLS DUE TO MANUAL BAILOUT

CROSS-REFERENCE TO RELATED APPLICATIONS

This application is a continuation of U.S. patent application Ser. No. 17/563,530, entitled "Disabling Surgical Tools Due to Manual Bailout," filed Dec. 28, 2021, and issued as U.S. Pat. No. 11,813,032 on Nov. 14, 2023, which is a continuation of U.S. patent application Ser. No. 16/427,818, entitled "Disabling Surgical Tools Due to Manual Bailout," filed May 31, 2019, and issued as U.S. Pat. No. 11,219,495 on Jan. 11, 2022.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Surgical staplers are one type of end effector capable of cutting and simultaneously stapling (fastening) transected tissue. Alternately referred to as an "endocutter," the surgical stapler includes opposing jaws capable of opening and closing to grasp and release tissue. Once tissue is grasped or clamped between the opposing jaws, the end effector may be "fired" to advance a cutting element or knife distally to transect grasped tissue. As the cutting element advances, staples contained within the end effector are progressively deployed to seal opposing sides of the transected tissue.

Some surgical tools include manual bailout mechanisms that allow a user to manually manipulate various portions of the tools in the event of an emergency, such as a loss of power or malfunction of the tool. For example, some surgical staplers include manual bailout mechanisms that enable a user to manually open the jaws or retract a knife. With some types of surgical tools, however, manually bailing out the surgical tool can damage internal gearing and may otherwise require that the surgical tool be precisely reset before subsequent use. What is needed is a way to accurately track when a surgical tool is subjected to a manual bailout.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgery and, more particularly, to systems and methods of disabling a surgical tool due to manual bailout of the surgical tool.

The embodiments described herein discuss manual bailout systems of surgical tools used in robotic surgery. The systems and methods may operate on Boolean logic. In a first method the torque and/or the motion of a firing motor of a robotic surgical system may be monitored. If any unexpected torque and/or motion is detected while the surgical tool is connected to the robotic surgical system, a bailout Boolean value indicating bailout motion may be set to "true" and the surgical tool may be disabled. Unexpected torque and/or motion may occur before, during, or after firing the end effector of the surgical tool.

A second method ensures that any manual bailout following firing of the end effector is recorded and stored, even in the event of power loss in the robotic surgical system. In such embodiments, after the user commands the surgical tool to fire, the bailout Boolean value may be set to "true", thus indicating that the end effector was not properly retracted under robotic control. At the conclusion of the firing sequence, however, the bailout Boolean value will be set to "false", thus indicating that the end effector was properly retracted under robotic control. If the surgical tool is manually bailed out before the firing sequence is completed, such as in the event of a power loss, the bailout Boolean value remains "true". Once operation is restored to the surgical tool, the robotic surgical system may recognize that the surgical tool may have been bailed out. Alternatively, the surgical tool may be removed from the robotic surgical system with the bailout Boolean value remaining "true". Upon installing the surgical tool on a new robotic surgical system, the new robotic surgical system will recognize the bailout Boolean value as being set to "true", thus determining that the surgical tool was previously bailed out. In some applications, a visual display of the robotic surgical system may provide detailed instructions on how to deal with the surgical tool after having been bailed out.

Figure 1:
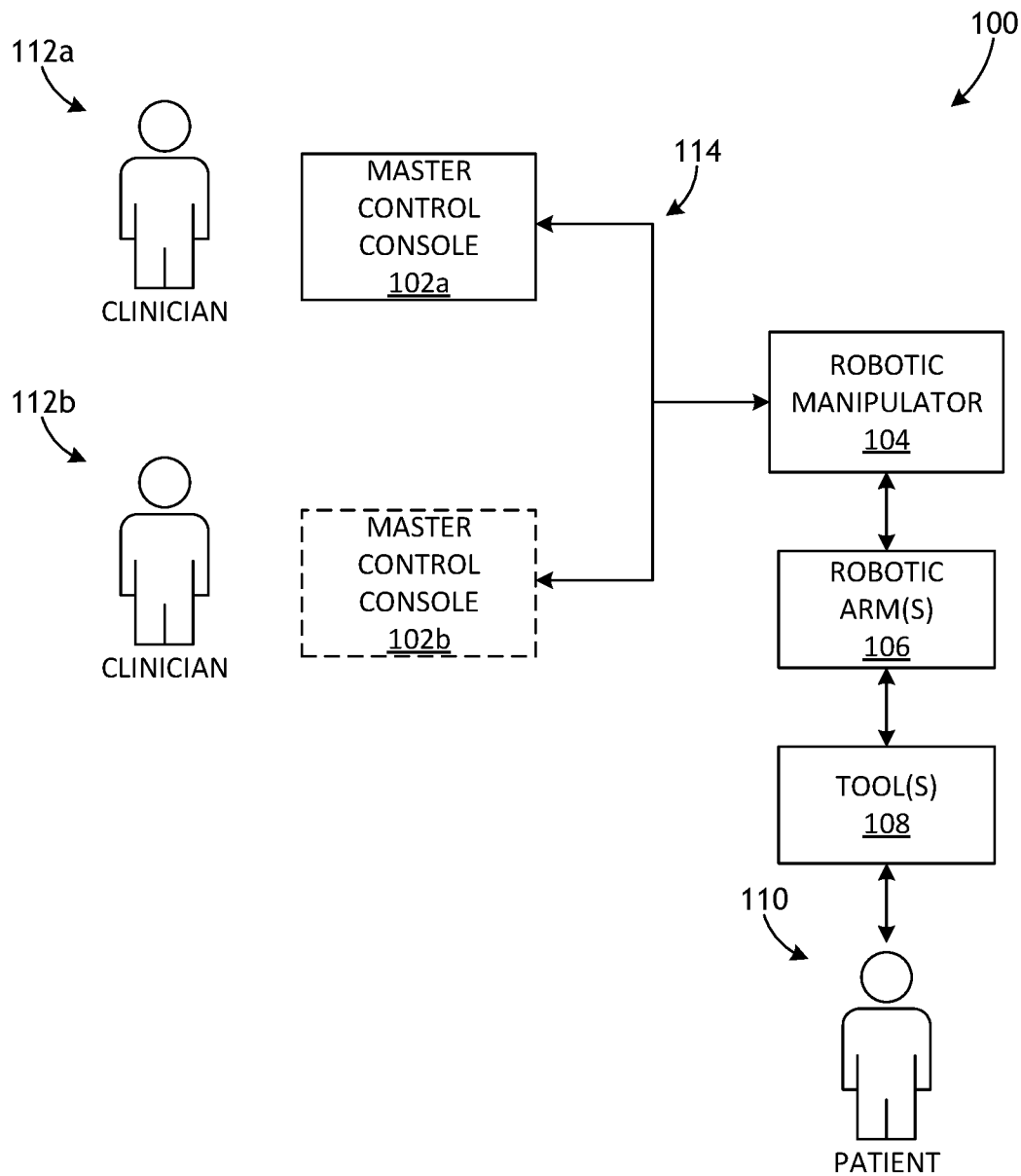
FIG. 1 is a block diagram of an example robotic surgical system that may incorporate some or all of the principles of the present disclosure.
Figure 3:
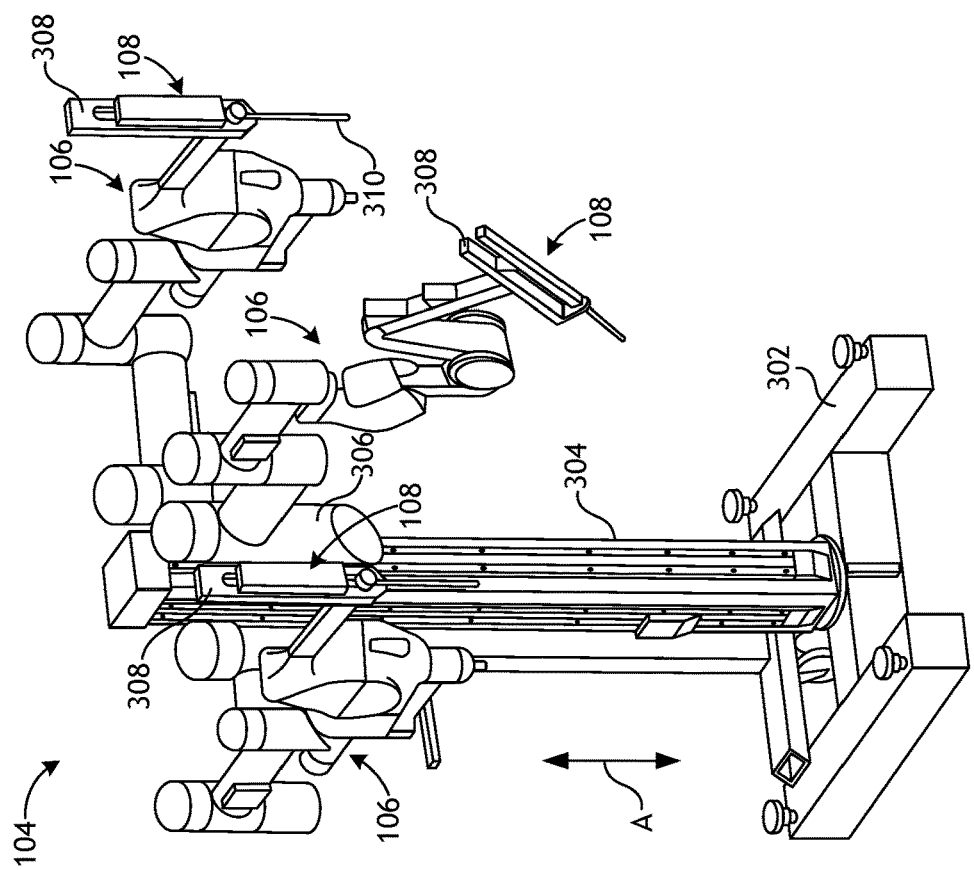
FIG. 3 depicts one example of the robotic manipulator of FIG. 1, according to one or more embodiments.
Figure 2:
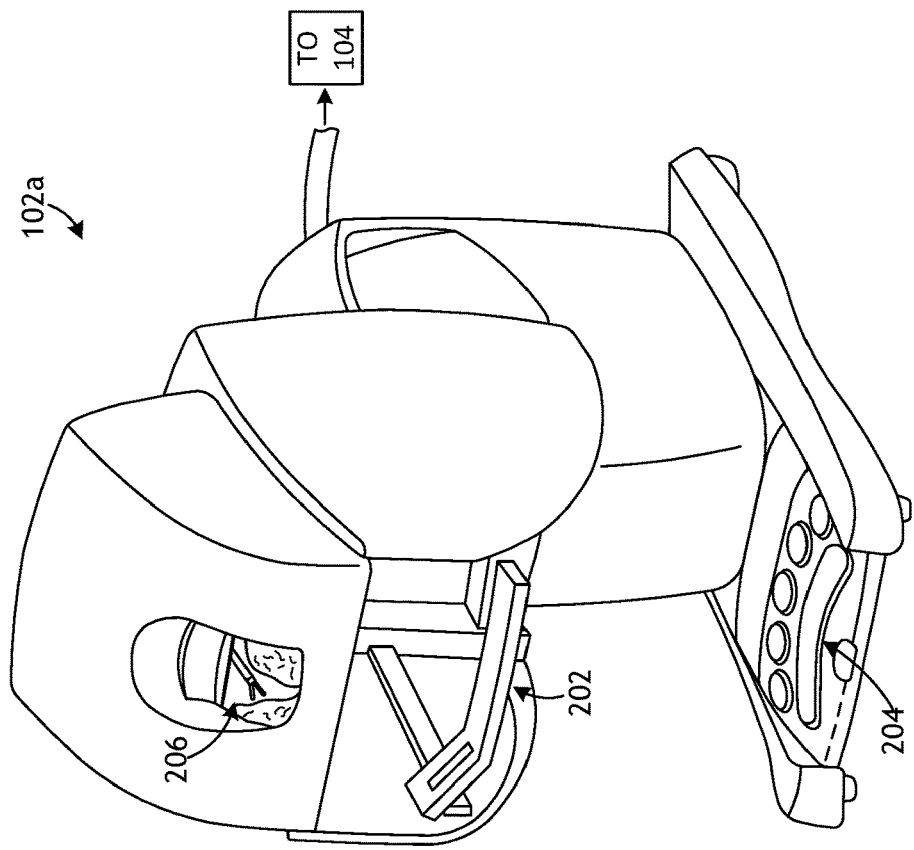
FIG. 2 is an example embodiment of one of the master control consoles of FIG. 1.

FIGS. 1-3 illustrate the structure and operation of an example robotic surgical system and associated components thereof. While applicable to robotic surgical systems, it is noted that the principles of the present disclosure may alternatively be applied to non-robotic surgical systems, without departing from the scope of the disclosure.

FIG. 1 is a block diagram of an example robotic surgical system 100 that may incorporate some or all of the principles of the present disclosure. As illustrated, the system 100 can include at least one master control console 102a and at least one robotic manipulator 104. The robotic manipulator 104 may be mechanically and/or electrically coupled to or otherwise include one or more robotic arms 106. In some embodiments, the robotic manipulator 104 may be mounted to a transport cart (alternately referred to as an "arm cart") that enables mobility of the robotic manipulator 104 and the associated robotic arms 106. Each robotic arm 106 may include and otherwise provide a tool driver where one or more surgical instruments or tools 108 may be mounted for performing various surgical tasks on a patient 110. Operation of the robotic arms 106, the corresponding tool drivers, and the associated tools 108 may be directed by a clinician 112a (e.g., a surgeon) from the master control console 102a.

In some embodiments, a second master control console 102b (shown in dashed lines) operated by a second clinician 112b may also help direct operation of the robotic arms 106 and the tools 108 in conjunction with the first clinician 112a. In such embodiments, for example, each clinician 112a,b may control different robotic arms 106 or, in some cases, complete control of the robotic arms 106 may be passed between the clinicians 112a,b. In some embodiments, additional robotic manipulators having additional robotic arms may be utilized during surgery on a patient 110, and these additional robotic arms may be controlled by one or more of the master control consoles 102a,b.

The robotic manipulator 104 and the master control consoles 102a,b may communicate with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Accordingly, the clinicians 112a,b may be able to remotely control operation of the robotic arms 106 via the communications link 114, thus enabling the clinicians 112a,b to operate on the patient 110 remotely.

FIG. 2 is one example embodiment of the master control console 102a that may be used to control operation of the robotic manipulator 104 of FIG. 1. As illustrated, the master control console 102a can include a support 202 on which the clinician 112a,b (FIG. 1) can rest his/her forearms while gripping two user input devices (not shown), one in each hand. The user input devices can comprise, for example, physical controllers such as, but not limited to, a joystick, exoskeletal gloves, a master manipulator, etc., and may be movable in multiple degrees of freedom to control the position and operation of the surgical tool(s) 108 (FIG. 1). The master control console 102a may further include one or more foot pedals 204 engageable by the clinician 112a,b to change the configuration of the surgical system and/or generate additional control signals to control operation of the surgical tool(s) 108.

The user input devices and/or the foot pedals 204 may be manipulated while the clinician 112a,b (FIG. 1) views the procedure via a visual display 206. Images displayed on the visual display 206 may be obtained from an endoscopic camera or "endoscope." In some embodiments, the visual display 206 may include or otherwise incorporate a force feedback meter or "force indicator" that provides the clinician 112a,b with a visual indication of the magnitude of force being assumed by the surgical tool (i.e., a cutting instrument or dynamic clamping member) and in which direction. As will be appreciated, other sensor arrangements may be employed to provide the master control console 102a with an indication of other surgical tool metrics, such as whether a staple cartridge has been loaded into an end effector or whether an anvil has been moved to a closed position prior to firing, for example.

FIG. 3 depicts one example of the robotic manipulator 104 that may be used to operate a plurality of surgical tools 108, according to one or more embodiments. As illustrated, the robotic manipulator 104 may include a base 302 that supports a vertically extending column 304. A plurality of robotic arms 106 (three shown) may be operatively coupled to the column 304 at a carriage 306 that can be selectively adjusted to vary the height of the robotic arms 106 relative to the base 302, as indicated by the arrow A.

The robotic arms 106 may comprise manually articulable linkages, alternately referred to as "set-up joints." In the illustrated embodiment, a surgical tool 108 is mounted to corresponding tool drivers 308 provided on each robotic arm 106. Each tool driver 308 may include one or more drivers or motors used to interact with a corresponding one or more drive inputs of the surgical tools 108, and actuation of the drive inputs causes the associated surgical tool 108 to operate.

One of the surgical tools 108 may comprise an image capture device 310, such as an endoscope, which may include, for example, a laparoscope, an arthroscope, a hysteroscope, or may alternatively include some other imaging modality, such as ultrasound, infrared, fluoroscopy, magnetic resonance imaging, or the like. The image capture device 310 has a viewing end located at the distal end of an elongate shaft, which permits the viewing end to be inserted through an entry port into an internal surgical site of a patient's body. The image capture device 310 may be communicably coupled to the visual display 206 (FIG. 2) and capable of transmitting images in real-time to be displayed on the visual display 206.

The remaining surgical tools may be communicably coupled to the user input devices held by the clinician 112a,b (FIG. 1) at the master control console 102a (FIG. 2). Movement of the robotic arms 106 and associated surgical tools 108 may be controlled by the clinician 112a,b manipulating the user input devices. As described in more detail below, the surgical tools 108 may include or otherwise incorporate an end effector mounted on a corresponding articulable wrist pivotally mounted on a distal end of an associated elongate shaft. The elongate shaft permits the end effector to be inserted through entry ports into the internal surgical site of a patient's body, and the user input devices also control movement (actuation) of the end effector.

In use, the robotic manipulator 104 is positioned close to a patient requiring surgery and is then normally caused to remain stationary until a surgical procedure to be performed has been completed. The robotic manipulator 104 typically has wheels or casters to render it mobile. The lateral and vertical positioning of the robotic arms 106 may be set by the clinician 112a,b (FIG. 1) to facilitate passing the elongate shafts of the surgical tools 108 and the image capture device 310 through the entry ports to desired positions relative to the surgical site. When the surgical tools 108 and image capture device 310 are so positioned, the robotic arms 106 and carriage 306 can be locked in position.

Figure 4:
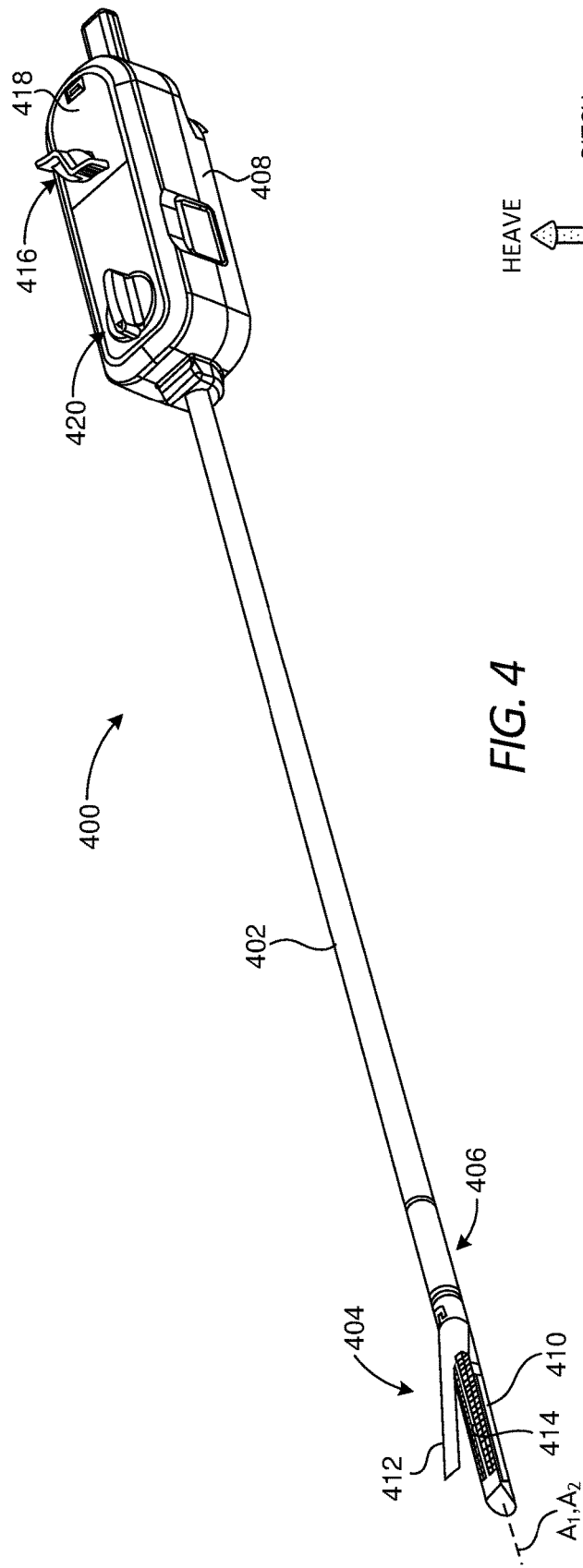
FIG. 4 is an isometric side view of an example surgical tool that may incorporate some or all of the principles of the present disclosure.

FIG. 4 is an isometric side view of an example surgical tool 400 that may incorporate some or all of the principles of the present disclosure. The surgical tool 400 may be the same as or similar to at least one of the surgical tools 108 of FIGS. 1 and 3 and, therefore, may be used in conjunction with a robotic surgical system, such as the robotic surgical system 100 of FIG. 1. As illustrated, the surgical tool 400 includes an elongated shaft 402, an end effector 404, an articulable wrist 406 (alternately referred to as a "wrist joint") that couples the end effector 404 to the distal end of the shaft 402, and a drive housing 408 coupled to the proximal end of the shaft 402. In applications where the surgical tool 400 is used in conjunction with a robotic surgical system, the drive housing 408 can include coupling features that releasably couple the surgical tool 400 to the robotic surgical system. The principles of the present disclosure, however, are equally applicable to surgical tools that are non-robotic and otherwise capable of manual manipulation.

The terms "proximal" and "distal" are defined herein relative to a robotic surgical system having an interface configured to mechanically and electrically couple the surgical tool 400 (e.g., the drive housing 408) to a robotic manipulator. The term "proximal" refers to the position of an element closer to the robotic manipulator and the term "distal" refers to the position of an element closer to the end effector 404 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 400 can have any of a variety of configurations capable of performing one or more surgical functions. In the illustrated embodiment, the end effector 404 comprises a surgical stapler, alternately referred to as an "endocutter," configured to cut and staple (fasten) tissue. As illustrated, the end effector 404 includes opposing jaws 410, 412 configured to move (articulate) between open and closed positions. The opposing jaws 410, 412, however, may alternately form part of other types of end effectors that include jaws such as, but not limited to, tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. One or both of the jaws 410, 412 may be configured to pivot to actuate the end effector 404 between the open and closed positions. In the illustrated example, the second jaw 412 is rotatable (pivotable) relative to the first jaw 410 to move between an open, unclamped position and a closed, clamped position. In other embodiments, however, the first jaw 410 may move (rotate) relative to the second jaw 412, without departing from the scope of the disclosure.

In the illustrated example, the first jaw 410 may be characterized or otherwise referred to as a "cartridge" jaw, and the second jaw 412 may be characterized or otherwise referred to as an "anvil" jaw. The first jaw 410 may include a frame that houses or supports a staple cartridge, and the second jaw 412 is pivotally supported relative to the first jaw 410 and defines a surface that operates as an anvil to deform staples ejected from the staple cartridge during operation.

Figure 5:
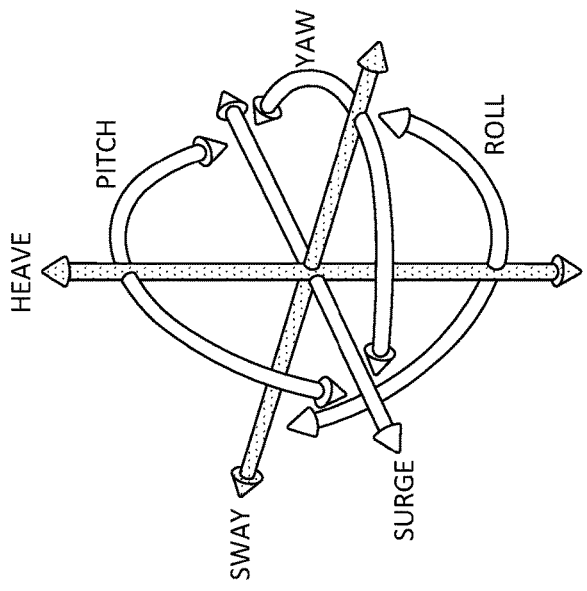
FIG. 5 illustrates potential degrees of freedom in which the wrist of FIG. 4 may be able to articulate (pivot).

The wrist 406 enables the end effector 404 to articulate (pivot) relative to the shaft 402 and thereby position the end effector 404 at desired orientations and locations relative to a surgical site. FIG. 5 illustrates the potential degrees of freedom in which the wrist 406 may be able to articulate (pivot). The wrist 406 can have any of a variety of configurations. In general, the wrist 406 comprises a joint configured to allow pivoting movement of the end effector 404 relative to the shaft 402. The degrees of freedom of the wrist 406 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 404) with respect to a given reference Cartesian frame. As depicted in FIG. 5, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 406 (e.g., X-axis), yaw movement about a second axis of the wrist 406 (e.g., Y-axis), and combinations thereof to allow for 360° rotational movement of the end effector 404 about the wrist 406. In other applications, the pivoting motion can be limited to movement in a single plane, e.g., only pitch movement about the first axis of the wrist 406 or only yaw movement about the second axis of the wrist 406, such that the end effector 404 moves only in a single plane.

Referring again to FIG. 4, the surgical tool 400 may incorporate or include an actuation system designed to facilitate articulation of the wrist 406 and actuation (operation) of the end effector 404 (e.g., clamping, firing, rotation, articulation, energy delivery, etc.). The actuation system may include a plurality of drive members or the like (obscured in FIG. 4) that extend from the drive housing 408 to the wrist 406, and selective actuation of these drive members causes the end effector 404 to articulate (pivot) relative to the shaft 402 at the wrist 406. The end effector 404 is depicted in FIG. 4 in the unarticulated position where a longitudinal axis $A_2$ of the end effector 404 is substantially aligned with the longitudinal axis $A_1$ of the shaft 402, such that the end effector 404 is at a substantially zero angle relative to the shaft 402. In the articulated position, the longitudinal axes $A_1$, $A_2$ would be angularly offset from each other such that the end effector 404 is at a non-zero angle relative to the shaft 402.

Other drive members may extend to the end effector 404, and selective actuation of those drive members may cause the end effector 404 to actuate (operate). Actuating the end effector 404 may include closing and/or opening the second jaw 412 relative to the first jaw 410 (or vice versa), thereby enabling the end effector 404 to grasp (clamp) onto tissue. Once tissue is grasped or clamped between the opposing jaws 410, 412, actuating the end effector 404 may further include "firing" the end effector 404, which may refer to causing a cutting element or knife (not visible) to advance distally within a slot 414 defined in the second jaw 410. As it moves distally, the cutting element may transect any tissue grasped between the opposing jaws 410, 412. Moreover, as the cutting element advances distally, a plurality of staples contained within the staple cartridge (e.g., housed within the first jaw 410) may be urged (cammed) into deforming contact with corresponding anvil surfaces (e.g., pockets) provided on the second jaw 412. The deployed staples may form multiple rows of staples that seal opposing sides of the transected tissue.

In some applications, the surgical tool 400 may also be configured to apply energy to tissue, such as radio frequency (RF) energy. In such cases, actuating the end effector 404 may further include applying energy to tissue grasped or clamped between two opposing jaws to cauterize or seal the captured tissue, following which the tissue may be transected.

The surgical tool 400 may further include one or more bailout mechanisms that allow a user to manually operate (manipulate) the surgical tool 400 in case of an emergency, such as a system malfunction or loss of power to the robotic surgical system. For example, the surgical tool 400 may include a manual knife bailout system that allows a user to manually retract the knife. The manual knife bailout system includes a key 416 accessible to a user to cause knife retraction. In the illustrated embodiment, the key 416 is located on the exterior of the drive housing 408 and may extend through a panel 418 of the drive housing 408 to be operatively coupled to internal gearing within the drive housing 408. A clinician may rotate the key 416 in a first direction (e.g., counter-clockwise) to manually retract the knife. In some embodiments, key 416 and the associated gearing may be unidirectional and otherwise designed such that the key 416 ratchets when turned in a second direction (e.g., clockwise). In such embodiments, turning the key 416 in the second direction will not drive the gearing.

In at least one embodiment, the panel 418 may be removable and the key 416 may be contained (stored) within drive housing 408. In such embodiments, the panel 418 may be removed to expose the key 416 and the clinician may then be able to attach the key 416 to the gearing for operation. In other embodiments, however, the key 416 may be attached to or from part of the bottom (underside) of the panel 418. In such embodiments, the clinician may remove the panel 418 and align the key 416 with the associated gearing, thus converting the removable panel 418 into a type of wrench.

The surgical tool 400 may further include a manual jaw bailout system that enables a user to manually open and close the jaws 410, 412. In the illustrated embodiment, the manual jaw bailout system may include a bailout tool 420 accessible to a user on the exterior of the drive housing 408. The bailout tool 420 may be operatively coupled to various gears and/or drive members located within the drive housing 408 to allow a clinician to manually open and close the jaws 410, 412. By rotating the bailout tool 420 in either angular direction, a clinician may be able to fully clamp and fully unclamp the jaws 410, 412.

Figure 6:
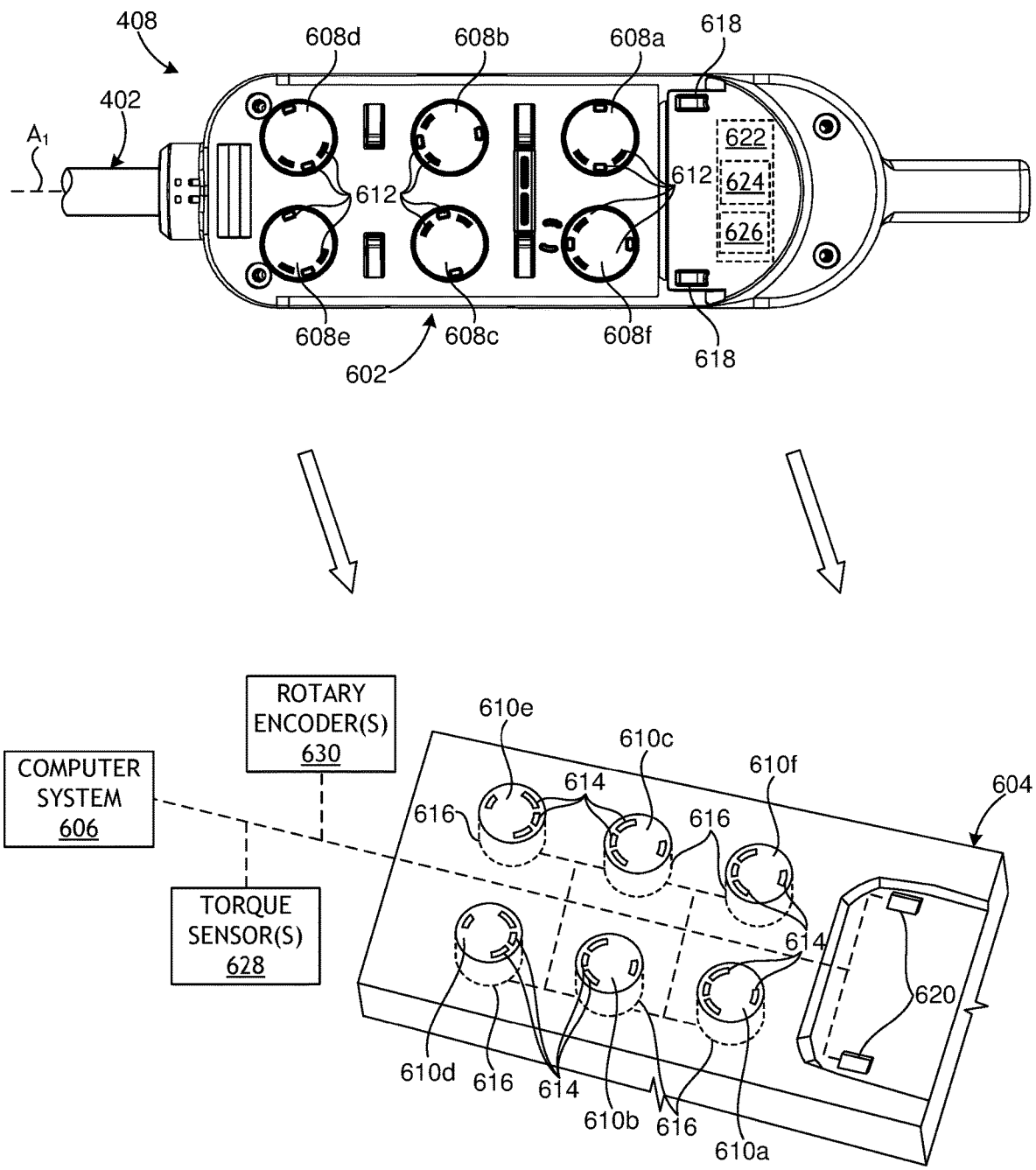
FIG. 6 is a bottom view of the drive housing of FIG. 4, according to one or more embodiments.

FIG. 6 is a bottom view of the drive housing 408, according to one or more embodiments. As illustrated, the drive housing 408 may include a tool mounting portion 602 used to operatively couple the drive housing 408 to a tool driver 604. The tool driver 604 may be the same as or similar to the tool drivers 308 of FIG. 3, and may thus be operable in conjunction with the robotic manipulator 104 of FIGS. 1 and 3. Mounting the drive housing 408 to the tool driver 604 places the drive housing 408 in communication with a computer system 606, which may communicate with or otherwise form part of the master controllers 102*a,b* (FIG. 1). The computer system 608 monitors and directs operation of the drive housing 408 via operation of the tool driver 604, thus enabling a user (e.g., the clinicians 112*a,b* of FIG. 1) to control operation of the drive housing 408 by working through the master controller 102*a,b*.

The tool mounting portion 602 includes and otherwise provides an interface that mechanically, magnetically, and/or electrically couples the drive housing 408 to the tool driver 604. In at least one embodiment, the tool mounting portion 602 couples the drive housing 408 to the tool driver 604 via a sterile barrier (not shown). As illustrated, the interface can include and support a plurality of inputs, shown as drive inputs 608*a*, 608*b*, 608*c*, 608*d*, 608*e*, and 608*f*. Each drive input 608*a-f* may comprise a rotatable disc configured to align (mate) with and couple to a corresponding driver 610*a*, 610*b*, 610*c*, 610*d*, 610*e*, and 610*f* of the tool driver 604. Each drive input 608*a-f* and corresponding driver 610*a-f* provide or define one or more matable surface features 612 and 614, respectively, configured to facilitate mating engagement between the opposing surface features 612, 614 such that movement (rotation) of a given driver 610*a-f* correspondingly moves (rotates) the associated drive input 608*a-f*.

Each driver 610*a-f* may include or otherwise comprise a motor 616 configured to actuate the corresponding driver 610*a-f*, and actuation of a given driver 610*a-f* correspondingly causes actuation of the mated drive input 608*a-f*, which facilitates operation of the mechanics of the drive housing 408. More specifically, actuation of the motors 616 may cause rotational movement of the corresponding driver 610*a-f*, which, in turn, rotates the associated drive input 608*a-f*. Each motor 616 may be in communication with the computer system 606 and, based on input signals provided by a user (e.g., a surgeon), the computer system 606 may selectively cause any of the motors 616 to actuate and thereby drive the corresponding driver 610*a-f*.

In some embodiments, actuation of the first drive input 608*a* via the first driver 610*a* may control rotation of the shaft 402 about its longitudinal axis $A_1$. Depending on the rotational direction of the first drive input 608*a*, the shaft 402 can be rotated clockwise or counter-clockwise, thus correspondingly rotating the end effector 404 (FIG. 4) in the same direction. Actuation of the second and third drive inputs 608*b,c* via the second and third drivers 610*a,b*, respectively, may control articulation of the end effector 404 at the wrist 406 (FIG. 4). Actuation of the fourth and fifth drive inputs 608*d,e* via the fourth and fifth drivers 610*d,e*, respectively, may cause an outer portion of the shaft 402 (referred to herein as a "closure tube") to advance and retract, which closes and opens the jaws 410, 412 (FIG. 4). Lastly, actuation of the sixth drive input 608*f* via the sixth driver 610*f* may cause the end effector 404 to fire, which may entail distal deployment of a cutting element to transect tissue grasped by the jaws 410, 412 and simultaneous deployment of staples contained within the staple cartridge housed within the first jaw 410.

The tool mounting portion 602 may further include one or more electrical connectors 618 (two shown) configured to mate with corresponding electrical connections 620 (two shown) provided by the tool driver 604 to facilitate communication between the drive housing 408 and the tool driver 604. Alternately, the drive housing 408 can wirelessly communicate with the tool driver 604, such as through a near field communication connection. The drive housing 408 may further house or otherwise include an internal computer 622 that may include a memory 624 and/or a microprocessor 626. The memory 624 may include one or more databases or libraries that store data relating to the drive housing 408 and, more particularly, to the surgical tool 400 (FIG. 4). In some embodiments, the memory 624 may include non-transitory, computer-readable media such as a read-only memory (ROM), which may be PROM, EPROM, EEPROM, or the like. Mating the drive housing 408 to the tool driver 604 places the internal computer 622 in communication with the computer system 606.

The computer system 606 may be programmed and otherwise configured to monitor operation of the surgical tool 400 (FIG. 4) using various sensors and/or electromechanical devices, collectively referred to herein as "monitoring devices." Each monitoring device may be designed to monitor one or more operational parameters of the surgical tool 400 and report measured operational parameters to the computer system 606 for processing. The computer system 606, for example, may be in communication with one or more torque sensors 628 and/or one or more rotary encoders 630, each of which may be characterized as a monitoring device designed to monitor operational parameters of the surgical tool 400. The torque sensors 628, for instance, may be configured to monitor torque, and the rotary encoders 630 may be configured to monitor motion (rotational or linear).

The torque sensors 628 and the rotary encoders 630 may be incorporated into the motors 616 of some or all of the drivers 610a-f, but could alternatively be operatively coupled to one or more of the drive inputs 608a-f. The torque sensors 628 may be configured to measure the real-time torque loading on the motors 616, which corresponds to the torque loading assumed by the drivers 610a-f and/or the drive inputs 608a-f. The rotary encoders 630 may measure the rotational motion or output of the motors 616, which corresponds to the rotational motion of the drivers 610a-f and/or the drive inputs 608a-f. Monitoring torque loading and rotational motion of the motors 616 may help determine if the surgical tool 400 is operating in accordance with the commands provided by the computer system 606. More particularly, when the torque sensors 628 or the rotary encoders 630 detect (measure) a torque input or rotational motion (e.g., an operational parameter) that is inconsistent with commands given by the computer system 606, that may be an indication that the user has activated one of the bailout mechanisms that are operatively coupled to the drive inputs 608a-f. According to embodiments of the present disclosure, the computer system 606 may be programmed to recognize a manual bailout based on signals received from the torque sensors 628 and the rotary encoders 630, and alert a user when a tool (e.g., the surgical tool 400) has been manually bailed out.

Figure 7A:
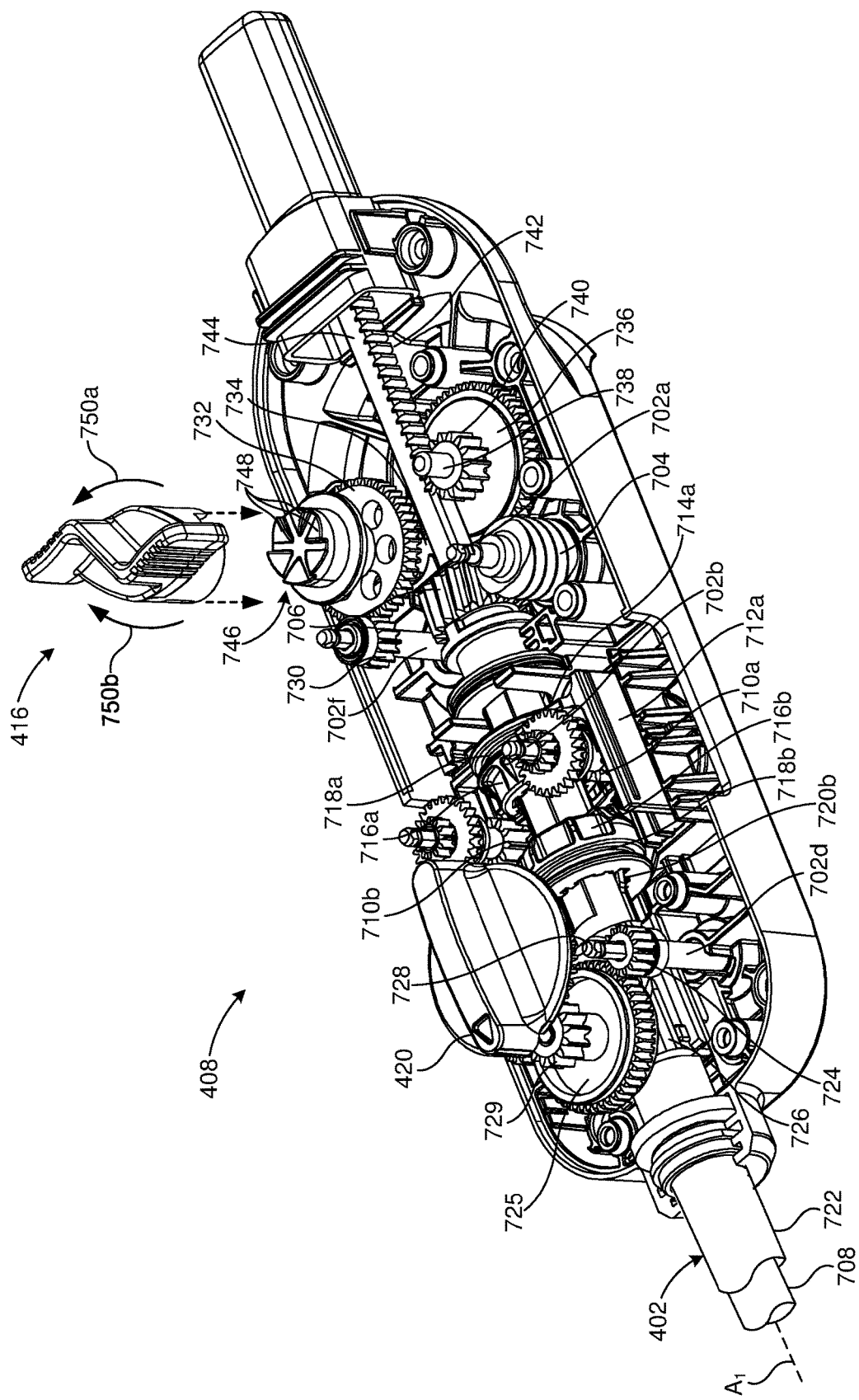
FIGS. 7A and 7B are exposed isometric views of the interior of the drive housing of FIG. 4, according to one or more embodiments.
Figure 7B:
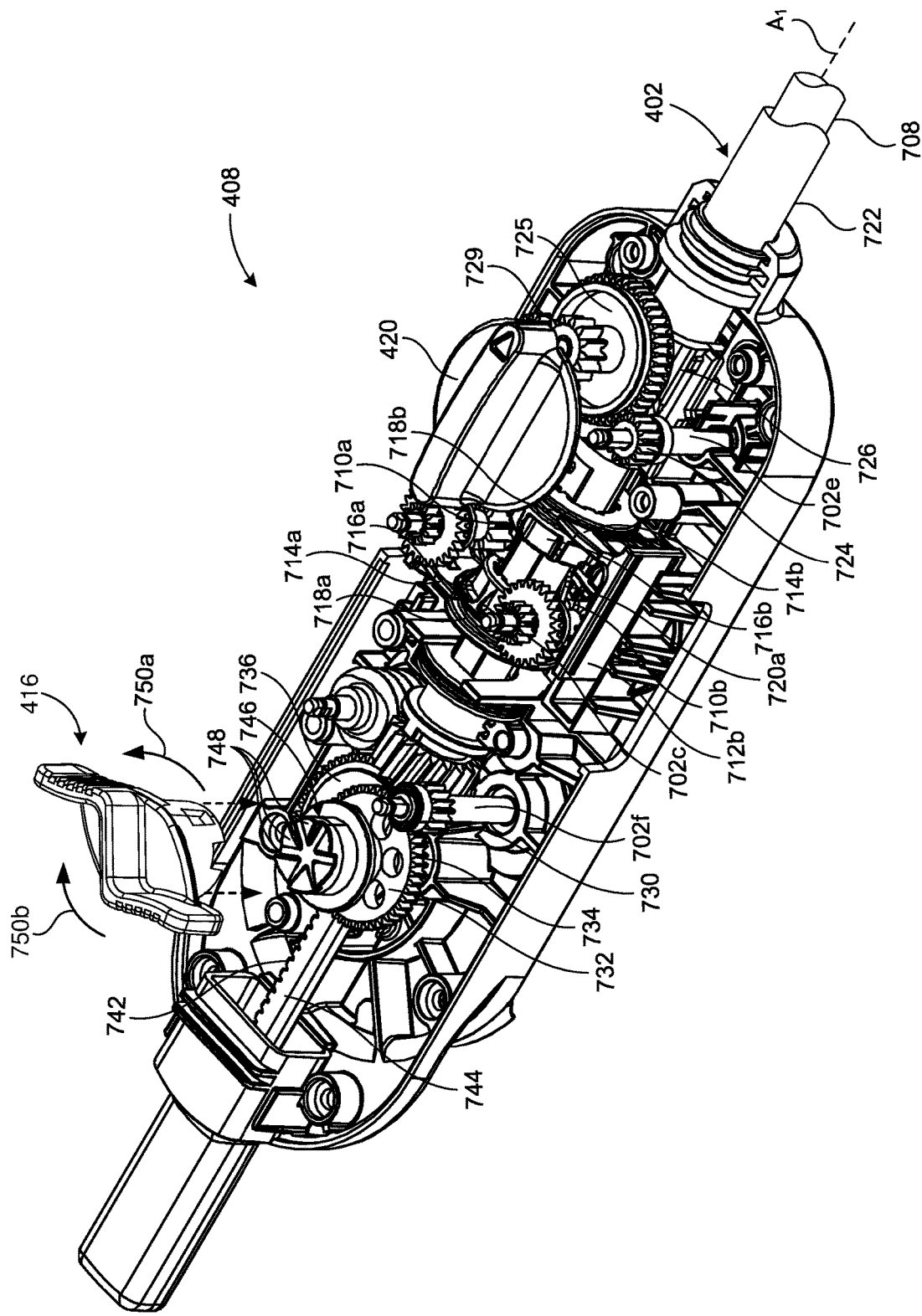

Referring to FIGS. 7A and 7B, illustrated are exposed isometric views of the interior of the drive housing 408, according to one or more embodiments. The upper portion of the drive housing 408 is omitted in FIGS. 7A-7B to allow viewing of the internal working components and parts. In addition, several component parts that would otherwise be included within the drive housing 408 are omitted in FIGS. 7A-7B to simplify the figures and enable discussion of the depicted component parts.

Referring first to FIG. 7A, a first drive shaft 702a is coupled to the first drive input 608a (FIG. 6) such that actuation and rotation of the first drive input 608a correspondingly rotates the first drive shaft 702a. A helical drive gear 704 is coupled to the first drive shaft 702a and rotates as the first drive shaft 702a rotates. The helical drive gear 704 intermeshes with a helical driven gear 706, which is operatively coupled to the shaft 402 and, more particularly, to an inner grounding shaft 708 that forms part of the shaft 402. The inner grounding shaft 708 extends concentrically within an outer portion of the shaft 402 referred to herein as the "closure tube." Accordingly, actuation of the first drive input 608a drives the first drive shaft 702a and correspondingly drives the inner grounding shaft 708 to rotate the shaft 402 about the longitudinal axis $A_1$.

A second drive shaft 702b may be coupled to the second drive input 608b (FIG. 6) such that actuation and rotation of the second drive input 608b correspondingly rotates the second drive shaft 702b. A pinion gear 710a (best seen in FIG. 7B) is attached to the second drive shaft 702b and is rotatable therewith. The pinion gear 710a intermeshes with a first driven rack 712a such that as the pinion gear 710a is rotated in a first rotational direction, the first driven rack 712a correspondingly translates in a first longitudinal direction. As the pinion gear 710a is rotated in a second rotational direction, the first driven rack 712a correspondingly translates in a second longitudinal direction opposite the first longitudinal direction.

The first driven rack 712a includes a first fork 714a (best seen in FIG. 7B) matable with a first articulation yoke 716a. More specifically, the first fork 714a is configured to be received within an annular slot 718a defined in the first articulation yoke 716a, which allows the first articulation yoke 716a to rotate about the longitudinal axis $A_1$ as the inner grounding shaft 708 rotates. Moreover, engagement between the first fork 714a and the annular slot 718a allows the first driven rack 712a to drive the first articulation yoke 716a along the longitudinal axis $A_1$ (distally or proximally) as acted upon by rotation of the second drive shaft 702b. As best seen in FIG. 7B, the first articulation yoke 716a may be coupled to a first drive member 720a, which extends distally to the wrist 406 (FIG. 4) along the shaft 402. Axial movement of the first articulation yoke 716a along the longitudinal axis $A_1$ correspondingly moves the first drive member 720a, which causes the wrist 406 and the end effector 404 (FIG. 4) to articulate.

Referring to FIG. 7B, a third drive shaft 702c is coupled to the third drive input 608c (FIG. 6) such that actuation and rotation of the third drive input 608c correspondingly rotates the third drive shaft 702c. A pinion gear 710b (best seen in FIG. 7A) is attached to the third drive shaft 702c and is rotatable therewith. The pinion gear 710b intermeshes with a second driven rack 712b such that rotating the pinion gear 710b in a first rotational direction correspondingly translates the second driven rack 712b in a first longitudinal direction. Rotating the pinion gear 710b in a second rotational direction correspondingly translates the second driven rack 712b in a second longitudinal direction opposite the first longitudinal direction.

The second driven rack 712b includes a second fork 714b matable with a second articulation yoke 716b. More particularly, the second fork 714b is configured to be received within an annular slot 718b (best seen in FIG. 7A) defined in the second articulation yoke 716b, which allows the second articulation yoke 716b to rotate about the longitudinal axis $A_1$ as the inner grounding shaft 708 rotates. Moreover, engagement between the second fork 714b and the annular slot 718b allows the second driven rack 712b to drive the second articulation yoke 716b along the longitudinal axis $A_1$ (distally or proximally) as acted upon by rotation of the third drive shaft 702c. As best seen in FIG. 7A, the second articulation yoke 716b may be coupled to a second drive member 720b, which extends distally to the wrist 406 (FIG. 4). Axial movement of the second articulation yoke 716b along the longitudinal axis $A_1$ correspondingly moves the second drive member 720b, which causes the wrist 406 and the end effector 404 (FIG. 4) to articulate.

Accordingly, axial movement of the first and second articulation yokes 716a,b along the longitudinal axis $A_1$ cooperatively actuates the drive members 720a,b and, thereby, articulates the end effector 404. In at least one embodiment, the first and second articulation yokes 716a,b antagonistically operate such that one of the articulation yokes 716a,b pulls one of the drive members 720a,b proximally while the other articulation yoke 716a,b pushes the other drive member 720a,b distally. However, the first and second articulation yokes 716a,b may alternatively be operated independently without the other being operated.

A fourth drive shaft 702d (FIG. 7A) and a fifth drive shaft 702e (FIG. 7B) may be coupled to the fourth and fifth drive inputs 604d,e (FIG. 6), respectively, such that actuation and rotation of the fourth and fifth drive inputs 604d,e correspondingly rotates the fourth and fifth drive shafts 702d,e. Rotation of the fourth and fifth drive shafts 702d,e may cause the jaws 410, 412 (FIG. 4) to move between open and closed positions. More specifically, the outer portion of the shaft 402 may comprise a closure tube 722 that is axially advanced or retracted by rotation of the fourth and fifth drive shafts 702d,e to move the jaws 410, 412 between open and closed positions.

As illustrated, each drive shaft 702d,e has a spur gear 724 attached thereto, and both spur gears 724 are positioned to mesh with a primary drive gear 725 mounted to a closure yoke 726. The closure yoke 726 is rotatably mounted to the closure tube 722 but fixed axially thereto. This allows the closure tube 722 to rotate as the inner grounding shaft 708 rotates, but also allows the closure yoke 726 to advance or retract the closure tube 722. A projection (not shown) extends from or is otherwise coupled to the closure yoke 726, and the projection interacts with the primary drive gear 725 to facilitate axial movement of the closure yoke 726. Accordingly, rotating the spur gears 724 causes the primary drive gear 725 to rotate, which correspondingly causes the closure yoke 726 and the interconnected closure tube 722 to axially translate.

The primary drive gear 725 may also be operatively coupled (either directly or indirectly) to the bailout tool 420 arranged on the exterior of the drive housing 408 and forming part of the manual jaw bailout system. As best seen in FIG. 7A, the bailout tool 420 may provide a drive gear 728 arranged on its underside, and the drive gear 728 may intermesh with a driven gear 729 operatively coupled to the primary drive gear 725. In example operation of the manual jaw bailout system, a user can rotate the bailout tool 420, which will correspondingly rotate the drive gear 728 against the driven gear 729, and thereby cause the primary drive gear 725 to rotate and move the closure yoke 426 distally and proximally to close and open the jaws 410, 412 (FIG. 4). Rotating the bailout tool 420 will also cause the primary drive gear 725 to rotate the spur gears 724, which may cause torque and/or motion of the fourth and fifth drive shafts 702d,e, respectively. Accordingly, operation of the manual jaw bailout system will also affect the torque and/or motion assumed by the fourth and fifth drive shafts 702d,e.

Figure 8:
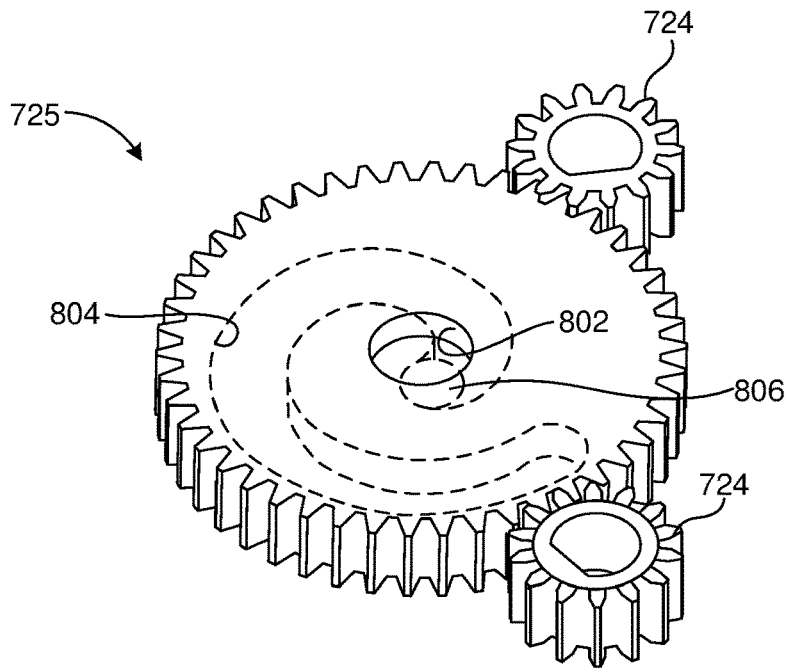
FIG. 8 is a schematic diagram of one example of the primary drive gear of FIGS. 7A-7B as intermeshed with the spur gears of FIGS. 7A-7B.

Referring briefly to FIG. 8, illustrated is one example of the primary drive gear 725 as intermeshed with the spur gears 724. As illustrated, the primary drive gear 725 comprises a central aperture 802 that rotatably mounts the primary drive gear 725 within the drive housing 408 (FIGS. 7A-7B) relative to the spur gears 724. A spiral cam slot 804 is defined in the primary drive gear 725 and sized to receive a projection 806 of the closure yoke 726 (FIGS. 7A-7B). The primary drive gear 725 is rotatable about an axis extending through the central aperture 802 as acted upon by the spur gears 724. As the primary drive gear 725 rotates, the projection 806 follows the spiral cam slot 804, and the curvature of the spiral cam slot 804 urges the interconnected closure yoke 726 to translate longitudinally relative to the primary drive gear 725. When the closure yoke 726 moves distally, the closure tube 722 (FIGS. 7A-7B) correspondingly moves in the distal direction and causes the jaws 410, 412 (FIG. 4) to close. In contrast, when the closure yoke 726 moves proximally, the closure tube 722 correspondingly moves in the proximal direction and causes the jaws 410, 412 to open.

Referring again to FIGS. 7A and 7B, a sixth drive shaft 702f is coupled to the sixth drive input 608f (FIG. 6) such that actuation and rotation of the sixth drive input 608f correspondingly rotates the sixth drive shaft 702f. Rotating the sixth drive shaft 702f may advance and retract a firing rod (not shown) that extends through the shaft 402 to the end effector 404 (FIG. 4). The cutting element (knife) may be operatively coupled to the distal end of the firing rod such that axial movement of the firing rod correspondingly moves the cutting element distally or proximally to transect tissue grasped between the jaws 410, 412 (FIG. 4). In some embodiments, distal movement of the firing rod also deploys a series of surgical staples, as described above.

A spur gear 730 is coupled to the sixth drive shaft 702f such that rotation of the sixth drive shaft 702f correspondingly rotates the spur gear 730. The spur gear 730 intermeshes with a second spur gear 732, which is attached to a first transfer drive shaft 734 (mostly occluded). A third spur gear (not visible) is attached to the bottom of the first transfer drive shaft 734 and intermeshes with a fourth spur gear 736, which is attached to a second transfer drive shaft 738 (FIG. 7A). Finally, an output pinion gear 740 (FIG. 7A) is coupled to the second transfer drive shaft 738 and intermeshes with a rack gear 742 of a firing member 744 such that rotation of the output pinion gear 740 causes axial translation of the firing member 744. The firing member 744 may be coupled to the firing rod generally described above. Accordingly, rotation of the sixth drive shaft 702f drives the firing member 744 in axial translation, which correspondingly drives the firing rod in the same direction to advance and retract the cutting element at the end effector 404 (FIG. 4).

The manual knife bailout system described above may include a bailout cap 746 operatively coupled to the first transfer drive shaft 734 such that rotation of the bailout cap 746 will correspondingly rotate the first transfer drive shaft 734, and vice versa. The bailout cap 746 may be matable with the key 416 and may include one or more surface features 748 configured to interact with corresponding engagement features (not shown) provided by the key 416. As illustrated, each surface feature 748 may be ramped in one angular direction and terminate at a raised shoulder. The engagement features of the key 416 may be configured to engage the raised shoulders when the key 416 is rotated in a first direction 750a (e.g., counter-clockwise), and ratchet over the surface features 748 when the key 416 is rotated in a second direction 750b (e.g., clockwise). Accordingly, the bailout cap 746 may operate as a unidirectional transfer member.

In example operation of the manual knife bailout system, a user rotating the key 416 in the first direction 750a will drive the bailout cap 746 to rotate the first transfer drive shaft 734 in the same direction. Because of the gearing interconnection between the first transfer drive shaft 734 and the firing member 744, as described above, rotation of the first transfer drive shaft 734 will correspondingly cause the firing member 744 to move in the first direction 750a and thereby retract the cutting element at the end effector 404 (FIG. 4). In contrast, when the key 416 is rotated by the user in the second direction 750b, the key 416 will ratchet over the surface features 748 and otherwise rotate relative to the bailout cap 746 and the first transfer drive shaft 734. Rotating the key 416 in the first direction 750a will also cause the second spur gear 732 to drive the spur gear 730 attached to the sixth drive shaft 702f, which may cause torque and/or motion of the sixth drive shaft 702f. Accordingly, operation of the manual knife bailout system may also affect the torque and/or motion assumed by sixth drive shaft 702f.

Referring again to FIG. 6 with continued reference to FIGS. 7A-7B, one or more of the torque sensors 628 and the rotary encoders 630 may be arranged to monitor operational parameters (e.g., torque, motion, or both) of the motors 616 that drive the fourth, fifth and sixth drivers 610d-f of the tool driver 604, which are operatively interconnected to the manual jaw and knife bailout systems. More specifically, the fourth and fifth drive shafts 702d,e are interconnected to the fourth and fifth drivers 610d,e through the fourth and fifth drive inputs 608d,e, respectively. Consequently, any torque or motion assumed by the fourth and fifth drive shafts 702d,e caused by activation of the manual jaw bailout system, as generally described above, will be detectable (measurable) at the motors 616 that drive the fourth and fifth drivers 610d,e, respectively. Similarly, the sixth drive shaft 702f is interconnected to the sixth driver 610f through the sixth drive input 608f. Consequently, any torque or motion assumed by the sixth drive shaft 702f caused by activation of the manual knife bailout system, as generally described above, will be detectable (measureable) at the motor 616 that drives the sixth driver 610f.

Accordingly, if a user activates the manual jaw bailout system, as generally described above, the torque sensors 628 and the rotary encoders 630 associated with the motors 616 that drive the fourth and fifth drivers 610d,e will measure an unexpected change in the operational parameters (e.g., torque, motion, or both) that is inconsistent with commands provided by the computer system 606. This provides a positive indication that the user has manually rotated the bailout tool 420 to activate the manual jaw bailout system. Similarly, if a user activates the manual knife bailout system, as generally described above, the torque sensor 628 and the rotary encoder 730 associated with the motor 616 that drives the sixth driver 610f will measure an unexpected change in the operational parameters (e.g., torque, motion, or both) that is inconsistent with commands provided by the computer system 606. This provides a positive indication that the user has manually rotated the key 416 to activate the manual knife bailout system.

Signals representative of unexpected change(s) to the torque and/or the motion of the motors 616 (collectively referred to as "bailout signals") may be transmitted to the computer system 606 for processing. In some embodiments, the computer system 606 may be programmed to disable the surgical tool 400 (FIG. 4) when a bailout signal is received. In other embodiments, or in addition thereto, the computer system 606 may communicate with the internal computer 622, which stores the bailout signal(s) in the memory 624. In such embodiments, when the surgical tool 400 is coupled to a new robotic surgical system, the new robotic surgical system will recognize that the surgical tool 400 has been previously bailed out. In yet other embodiments, or in addition thereto, the computer system 606 may upload the bailout signals to a central database (e.g., a non-volatile memory or the cloud) that can be queried upon coupling the surgical tool 400 to a new robotic surgical system.

Figure 9:
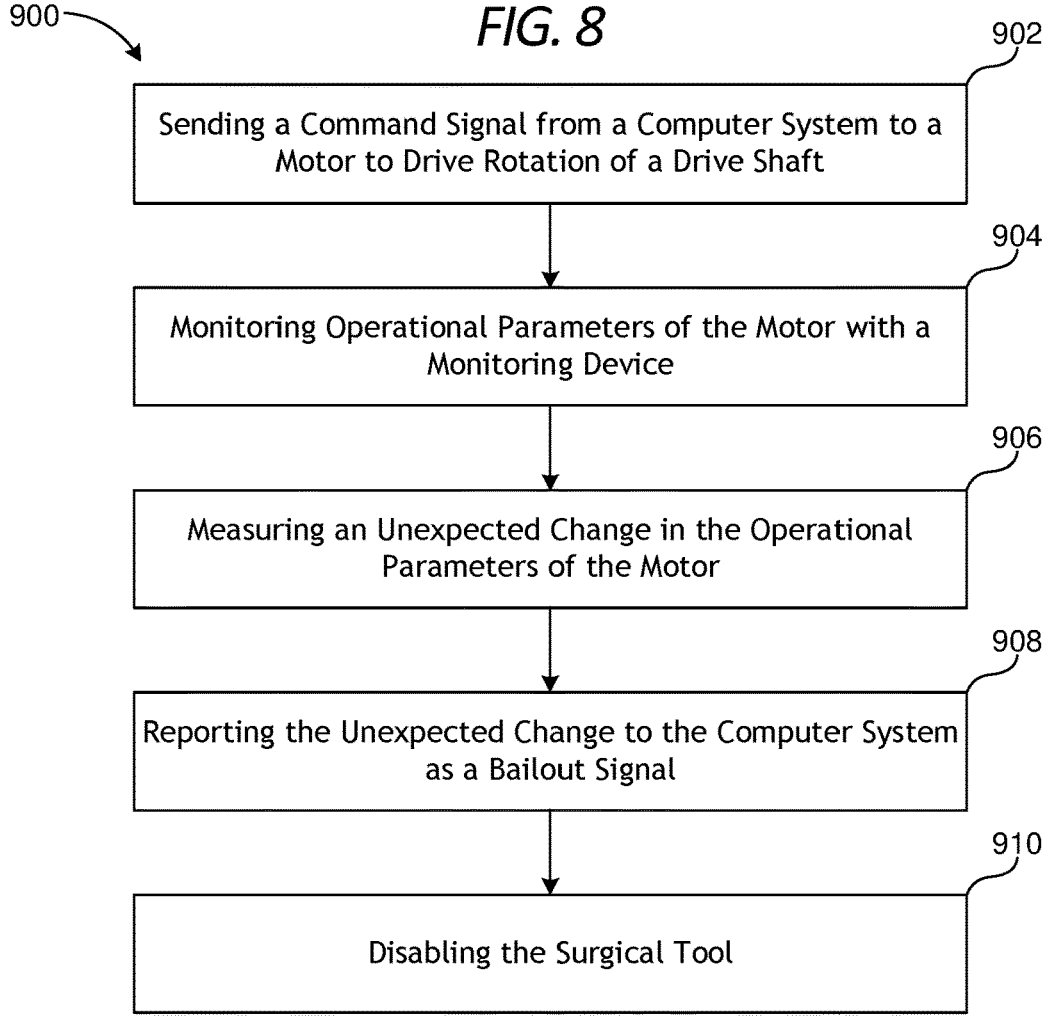
FIG. 9 is a flowchart diagram of an example method of operating the surgical tool of FIG. 4, according to one or more embodiments.

FIG. 9 is a flowchart diagram of an example method 900 of operating the surgical tool 400 of FIG. 4, according to one or more embodiments of the present disclosure. Discussion of the method 900 will refer to the components and systems of the surgical tool 400 described herein. Accordingly, the method 900 may be best understood with reference to the preceding figures and their description. As illustrated, the method 900 may include sending command signals from a computer system 606 (FIG. 6) to a motor 616 (FIG. 6) to drive rotation of a drive shaft 702d-f (FIG. 7), as at 902. As described above, the motor 616 may be operatively coupled to the drive shaft 702d-f via interconnection between the corresponding driver 610d-f (FIG. 6) and drive input 608d-f (FIG. 6) such that actuation of the motor 616 causes rotational movement of the corresponding drive shaft 702d-f. The rotational motion of the drive shaft 702d-f may cause articulation and/or actuation of the end effector 404 (FIG. 4) included in the surgical tool 400.

The method 900 may further include monitoring one or more operational parameters of the motor 616 with one or more monitoring devices, as at 904. The monitoring device(s) may comprise, for example, one or more of the torque sensors 628 (FIG. 6) and the rotary encoders 630 (FIG. 6), and the operational parameters may comprise at least one of torque and motion assumed by the motor 616 as operated by the computer system 606. During normal operation, the measured operational parameters of torque and rotational motion of the motor 616 will be consistent with the command signals provided by the computer system 606. In other words, the computer system 606 may be programmed to recognize and expect a predetermined magnitude of torque or motion based on a particular command signal provided to the motor 616. As long as the measured operational parameters are consistent with what is expected based on the command signals provided by the computer system 606, operation of the surgical tool 400 may proceed as normal.

The method 900 may further include measuring an unexpected change in the operational parameters of the motor 616 with the monitoring devices, as at 906. The unexpected change may comprise a measured torque or motion assumed by the motor 616 that is inconsistent with the command signal(s) provided by the computer system 606. Any unexpected changes may be reported to the computer system 606 as a bailout signal, as at 908. As described above, receipt of any bailout signal may be a positive indication that the user has activated one or both of the manual jaw or knife bailout systems. More specifically, the user may have rotated one or both of the key 416 (FIGS. 4 and 7A-7B) and the bailout tool 420 (FIGS. 4 and 7A-7B), and thereby rotated the corresponding drive shaft 702d-f interconnected thereto, and such rotation may be detected and measured by the torque sensors 628 and/or the rotary encoders 630 as an unexpected change to the torque and/or motion of the associated motor 616. As will be appreciated, an unexpected change to the torque and/or motion can occur before, during, or after the surgical tool 400 is fired (i.e., the knife is extended, etc.).

Once a bailout signal is received at the computer system 606, the method 900 may further include disabling the surgical tool 400, as at 910. In some embodiments, disabling the surgical tool 400 may comprise preventing the surgical tool 400 from further operation, thus rendering the surgical tool 400 unavailable (inoperable) for future procedures. Disabling the surgical tool 400 may allow the surgical tool 400 to retract and "home" the knife, but may simultaneously prevent the surgical tool 400 from being fired (i.e., extending the knife, etc.) again. In such embodiments, the robot may allow the user to open and close the device jaws 410, 412 (FIG. 4), roll (rotate) the shaft 402 (FIG. 4), and articulate the wrist 406, which may allow the user to easily remove the device from the patient.

In at least one embodiment, the user may be given the option to override the disabling function of the surgical tool 400. In other embodiments, or in addition thereto, disabling the surgical tool 400 may include communicating with the internal computer 622 (FIG. 6) of the drive housing 408 (FIG. 6) and storing the bailout signal(s) in the associated memory 624 (FIG. 6). This may prevent the surgical tool 400 from being used upon being coupled to a new robotic surgical system, which will automatically recognize that the surgical tool 400 was previously bailed out based on the bailout signals stored in the on-board memory 624. In yet other embodiments, or in addition thereto, the computer system 606 may upload the bailout signal to a central database (e.g., a non-volatile memory), such as the cloud. Upon coupling the surgical tool 400 to a new robotic surgical system, the new robotic surgical system will automatically recognize that the surgical tool 400 was previously bailed out based on the bailout signals stored in the central database.

Figure 10:
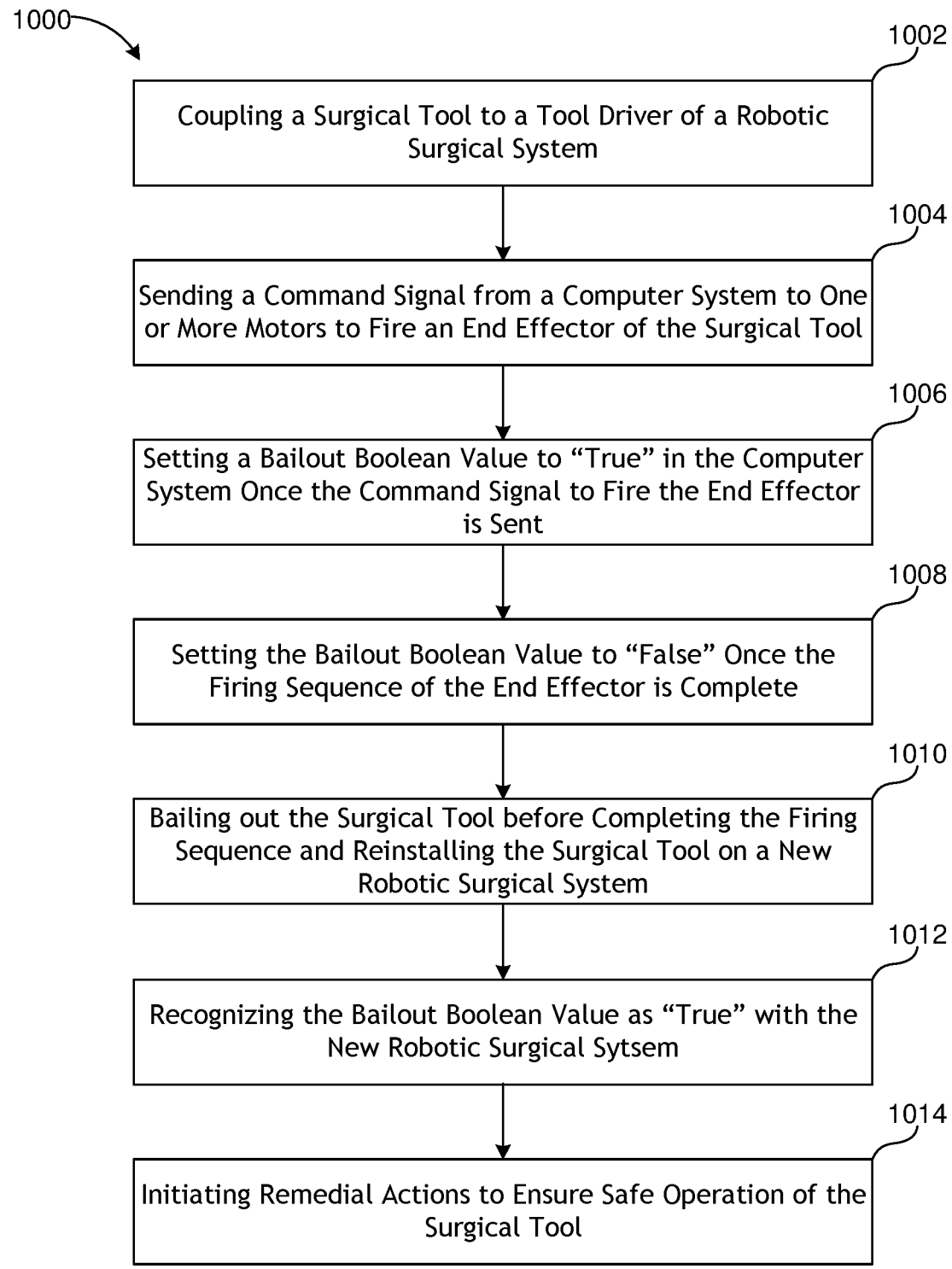
FIG. 10 is a flowchart diagram of another example method of operating the surgical tool of FIG. 4, according to one or more embodiments.

FIG. 10 is a flowchart diagram of another example method 1000 of operating the surgical tool 400 of FIG. 4, according to one or more additional embodiments. Similar to the method 900 of FIG. 9, discussion of the method 1000 will refer to the components and systems of the surgical tool 400 described herein. Accordingly, the method 1000 may be best understood with reference to the preceding figures and their description. As illustrated, the method 1000 may include coupling the surgical tool 400 to a tool driver 604 (FIG. 6) of a robotic surgical system, as at 1002. More specifically, the drive housing 408 (FIGS. 4 and 7A-7B) of the surgical tool 400 may be coupled to the tool driver 604, which causes the drive inputs 608a-f (FIG. 6) of the drive housing 408 to matingly engage the drivers 610a-f of the tool driver 604. Consequently, actuation of the drivers 610a-f will cause corresponding drive shafts 702a-f (FIGS. 7A-7B) coupled to each drive input 608a-f to rotate and thereby cause articulation and/or actuation of the end effector 404 (FIG. 4) of the surgical tool 400. As described above, each driver 610a-f may include a motor 616 (FIG. 6) in communication with a computer system 606 (FIG. 6) that controls operation of each motor 616, and thus controls operation of the surgical tool 400.

The method 1000 may further include sending a command signal from the computer system 606 to one or more of the motors 616 to fire the end effector 404, as at 904. More particularly, the command signal to fire the end effector 404 may be sent to the motor 616 operatively coupled to the sixth driver 610f, which causes rotation of the sixth drive input 608f (FIG. 6) and the interconnected sixth drive shaft 702f (FIGS. 7A-7B). As described above, rotating the sixth drive shaft 702f may cause axial translation of the firing member 744 (FIGS. 7A-7B), which causes the knife (cutting element) of the end effector 404 to advance or retract, depending on the rotational direction of the sixth driver 610f. Accordingly, firing the end effector 404 may entail distal advancement of the knife to transect tissue grasped by the jaws 410, 412 (FIG. 4) and simultaneous deployment of staples contained within the staple cartridge housed within the first jaw 410. Firing the end effector 404 may further include retracting the knife back to a "home" position, all done by robotic control.

In one or more embodiments, the computer system 606 may operate at least partially based in Boolean logic. In such embodiments, the method 1000 may further include setting a bailout Boolean value in the computer system 606 to "true" once the command signal is sent to fire the end effector 404, as at 1006. The method 1000 may further include setting the bailout Boolean value to "false" in the computer system 606 once the firing sequence of the end effector 404 is complete, as at 1008. The bailout Boolean value may provide the computer system 606 with an indication as to whether the surgical tool 400 has previously been bailed out or not during operation. Setting the bailout Boolean value to "false" in the computer system 606 indicates that the surgical tool 400 has not been previously bailed out. If the bailout Boolean value is set to "true," however, that indicates that the surgical tool 400 was previously bailed out. In some embodiments, the computer system 606 will communicate the bailout Boolean value to the internal computer 622 (FIG. 6) of the drive housing 408 (FIG. 6), and store the current bailout Boolean value, whether "true" or "false," in the associated memory 624 (FIG. 6).

In the present embodiment, setting the bailout Boolean value to "true" once the command signal is sent to fire the end effector 404 provides a safeguard in the event of an emergency, such as a loss of power or malfunction of the surgical tool 400 that requires the user to activate one of the manual jaw or knife bailout systems. During normal operation, firing the end effector 404 will be properly completed by the robotic surgical system and the associated motors 616, and the bailout Boolean value will be reset to "false" once the firing sequence is successfully completed under robotic control. However, if the surgical tool 400 is bailed out prior to completion of the firing sequence, and thus prior to properly retracting the knife under robotic control, the bailout Boolean value will remain set to "true". Once operation is restored to the surgical tool 400, the computer system 606 will automatically recognize that the surgical tool 400 may have been bailed out. In such embodiments, the computer system 606 may disable the surgical tool 400 so that it cannot be used in any further procedures. As indicated above, in disabling the surgical tool 400, the robot may still be able to retract and "home" the knife, but the surgical tool 400 may be prevented from being fired (i.e., extending the knife, etc.) once again. Moreover, the robot may allow the user to open and close the device jaws 410, 412 (FIG. 4), roll (rotate) the shaft 402 (FIG. 4), and articulate the wrist 406, which may allow the user to easily remove the device from the patient. The surgical tool 400 may then be removed from the robotic surgical system and decommissioned. Alternatively, the computer system 606 may generate an alert (e.g., audible, visual, tactile, etc.) to inform the user that the surgical tool 400 may have been previously bailed out, and the user may be given the option to override the alert and proceed with the operation or terminate the proceeding.

In other embodiments, the surgical tool 400 may be removed from the robotic surgical system following the occurrence of an emergency (e.g., loss of power, etc.). In such embodiments, upon installing the surgical tool 400 on a tool driver of a new robotic surgical system, the new robotic surgical system will query the memory 624 of the internal computer 622 and recognize the bailout Boolean value as being set to "true", thus determining that the surgical tool 400 was previously bailed out. Accordingly, the method 1000 may further include manually bailing out the surgical tool 400 before the firing sequence is complete and installing the surgical tool on a new robotic surgical system, as at 1010. The method 1000 further includes recognizing the bailout Boolean value as "true" with the new robotic surgical system, as at 1012. In such cases, a computer system (similar to the computer system 606) of the new robotic surgical system may be programmed to initiate one or more remedial actions to ensure safe operation of the surgical tool 400, as at 1014. One remedial action that may take place is disabling the surgical tool 400 so that it cannot be used in any further procedures. In such cases, the surgical tool 400 must be removed from the new robotic surgical system and decommissioned. Another remedial action may be to generate an alert (e.g., audible, visual, tactile, etc.) to inform the user that the surgical tool 400 has previously been bailed out. In at least one embodiment, the user may override the remedial action initiated by the new robotic surgical system or the remedial action may provide the user with an option to proceed or terminate the proceeding.

Figure 11:
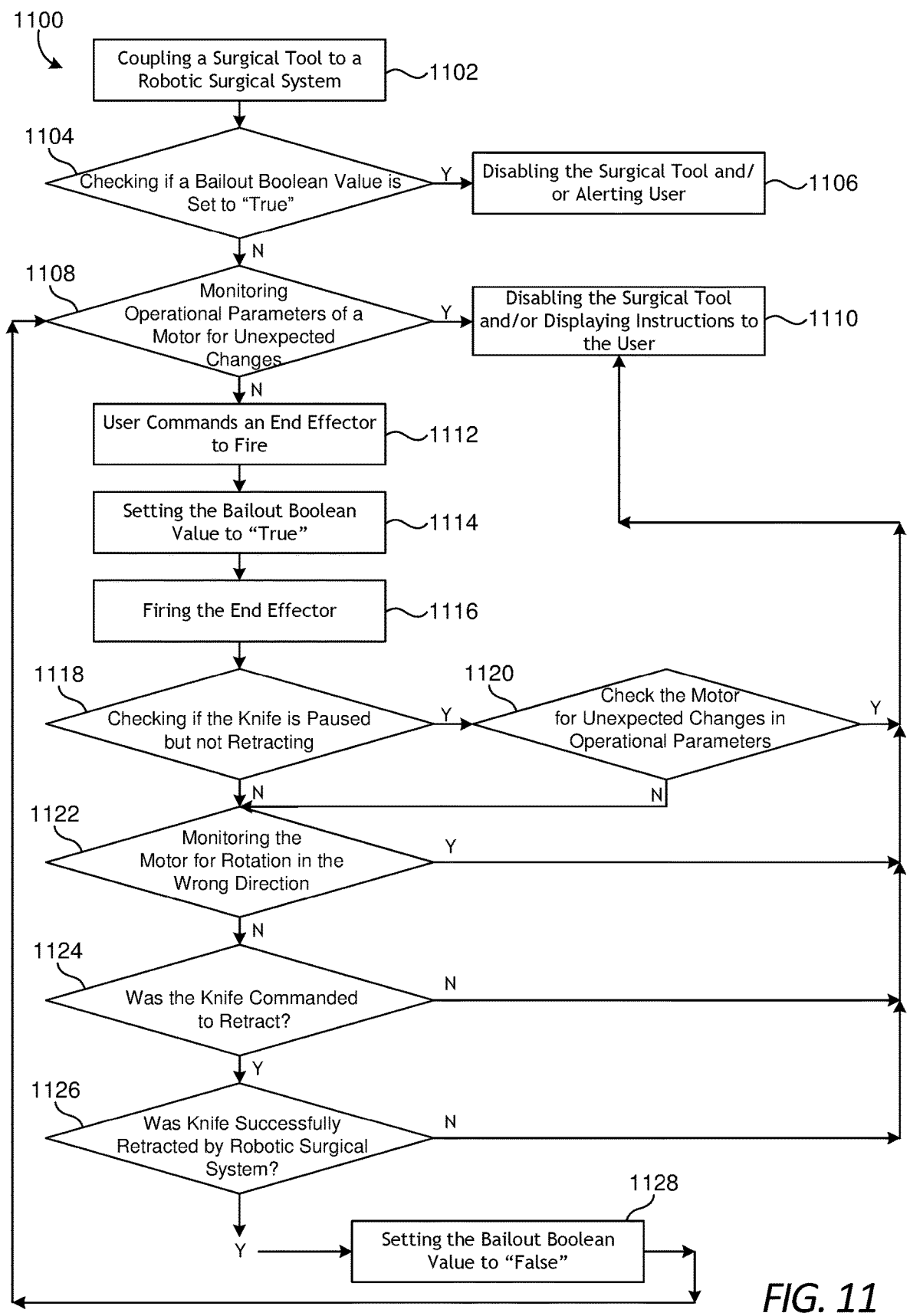
FIG. 11 is a flowchart diagram of another example method of operating the surgical tool of FIG. 4, according to one or more additional embodiments of the present disclosure.

FIG. 11 is a flowchart diagram of another example method 1100 of operating the surgical tool 400 of FIG. 4, according to one or more additional embodiments of the present disclosure. Similar to the methods 900 and 1000 of FIGS. 9 and 10, respectively, discussion of the method 1100 will refer to the components and systems of the surgical tool 400 described herein. Accordingly, the method 1100 may be best understood with reference to the preceding figures and their description. Moreover, similar to the method 1000, the method 1100 may be at least partially be based in Boolean logic.

The method 1100 may include coupling the surgical tool 400 to a robotic surgical system, as at 1102. More specifically, the drive housing 408 (FIGS. 4 and 7A-7B) of the surgical tool 400 may be coupled to the tool driver 604 (FIG. 6) of the robotic surgical system, which causes the drive inputs 608a-f (FIG. 6) of the drive housing 408 to matingly engage the drivers 610a-f of the tool driver 604. This also places the computer system 606 in communication with the internal computer 622 (FIG. 6) of the drive housing 408. The method 1100 may further include checking to see if the bailout Boolean value of the surgical tool 400 is set to "true", as at 1104. In some embodiments, this may entail the computer system 606 querying the memory 624 of the internal computer 622. In other embodiments, this may entail the computer system 606 querying a central database or the cloud, which may have the current bailout Boolean value for the surgical tool 400 uploaded thereon.

If the bailout Boolean value is set to "true", this may be an indication that the surgical tool 400 was previously bailed out and the method 1100 may include disabling the surgical tool 400 and/or alerting the user, as at 1106. Disabling the surgical tool 400 may prevent the user from using the surgical tool 400 unless proper remedial steps are taken to re-activate the surgical tool. Disabling the surgical tool 400 may allow the robot to retract and "home" the knife, but the surgical tool 400 may be prevented from being fired (i.e., extending the knife, etc.) once again. Otherwise, the surgical tool 400 must be removed from the robotic surgical system and decommissioned. In some embodiments, alerting the user may comprise generating an alert (e.g., audible, visual, tactile, etc.) to inform the user that the surgical tool 400 has previously been bailed out. In at least one embodiment, a visual message may appear on the visual display 206 (FIG. 2) and may indicate that the surgical tool 400 has been previously bailed out, and inquire as to whether the user wishes to proceed. Accordingly, the user may be able to override the disabling feature with an option to proceed or terminate the proceeding.

If the Boolean value is set to "false", however, the method 1100 may proceed by monitoring operational parameters of a motor 616 (FIG. 6) for one or more unexpected changes that indicate a bailout, as at 1008. More specifically, the computer system 606 may send command signals to the motor 616 (FIG. 6) to drive rotation of one of the drive shafts 702d-f (FIG. 7) operatively coupled to the motor 616 via interconnection between the corresponding driver 610d-f (FIG. 6) and drive input 608d-f (FIG. 6) such that actuation of the motor 616 causes rotational movement of the corresponding drive shaft 702d-f. The operational parameters of the motor 616 may be monitored with at least one of the torque sensors 628 (FIG. 6) and the rotary encoders 630 (FIG. 6). Accordingly, the operational parameters may comprise at least one of torque and rotational motion assumed by the motor 616 during operation. The measured operational parameters will be consistent with the command signals provided by the computer system 606 during normal operation. In contrast, an unexpected change to the operational parameters may comprise measured torque or motion that is inconsistent with the command signal(s) provided by the computer system 606, which may be a positive indication that the user has activated one or both of the manual jaw or knife bailout systems.

More specifically, the user may have rotated one or both of the key 416 (FIGS. 4 and 7A-7B) and the bailout tool 420 (FIGS. 4 and 7A-7B), and thereby rotated the corresponding drive shaft 702d-f, and such rotation may be detected and measured by the torque sensors 628 and/or the rotary encoders 630 as an unexpected change to the torque and/or motion of the associated motor 616. If an unexpected change to the operational parameters is detected, the bailout Boolean value is set to "true" and the surgical tool 400 is disabled, as at 1110. As indicated above, in disabling the surgical tool 400, the robot may still be able to retract and "home" the knife, but the surgical tool 400 may be prevented from being fired (i.e., extending the knife, etc.) once again. Moreover, if appropriate in the state of the procedure, the robot may allow the user to open and close the device jaws 410, 412 (FIG. 4), roll (rotate) the shaft 402 (FIG. 4), and articulate the wrist 406, which may allow the user to easily remove the device from the patient. In some embodiments, the method 1100 may further include displaying detailed instructions for the user, as also at 1110. The detailed instructions may appear on the visual display 206 (FIG. 2), for example, and may provide instructions on how to fully bail out the surgical tool 400 and remove the surgical tool 400 from the robotic surgical system, if necessary.

If no unexpected changes to the operational parameters of the motor 616 are detected, the user may proceed to command the end effector 404 of the surgical tool 400 to fire, as at 1112. Firing the end effector 404 may entail distal advancement of the knife to transect tissue grasped by the jaws 410, 412 (FIG. 4) and simultaneous deployment of staples contained within the staple cartridge housed within the first jaw 410. Once the command signal is sent to fire the end effector 404, the computer system 606 may simultaneously set the bailout Boolean value to "true", as at 1114, and then fire the surgical tool 400, as at 1116. As indicated above, setting the bailout Boolean value to "true" once the command signal is sent to fire the end effector 404 provides a safeguard in the event of an emergency that requires the user to activate one of the manual jaw or knife bailout systems. If the surgical tool 400 is bailed out prior to completing the commanded firing sequence, and thus prior to properly retracting the knife under robotic control, the bailout Boolean value will remain set to "true". Upon installing the surgical tool 400 on a tool driver of a new robotic surgical system, the new robotic surgical system will query the memory 624 of the internal computer 622 and recognize the bailout Boolean value as being set to "true". Accordingly, this helps the new robotic surgical system autonomously recognize that an incomplete firing may have occurred in the surgical tool 400, which may prompt remedial action.

During the firing sequence, the method 1100 may further include checking if the knife is paused but not retracting, as at 1118. More particularly, the computer system 606 may be programmed to monitor the operation of the motor 616 that causes firing of the end effector 404 throughout the firing sequence. If the torque sensors 628 and/or the rotary encoders 630 detect that the knife of the end effector 404 has stopped prior to completing the firing sequence, the computer system 606 may be programmed check the motor 616 for unexpected changes in operational parameters, as at 1120. If an unexpected change to the operational parameters is detected, that is an indication of user-activated bailout, and the method may proceed to disabling the surgical tool 400 and/or displaying detailed instructions for the user, as at 1110.

The method 1100 may further include monitoring the motor 616 for torque or motion in the wrong direction, as at 1122. If torque or motion of the motor 616 is detected in the wrong direction as compared to a proper firing sequence wholly under robotic control, then that may be an indication of a user-activated bailout, and the method may proceed to disabling the surgical tool 400 and/or displaying detailed instructions for the user, as at 1110. If there is no torque or motion detected in the wrong direction, the computer system 606 may be programmed to determine if the knife was commanded to retract, as at 1124. If the knife was not commanded to retract, then that may be an indication of user-activated bailout, and the method may proceed to disabling the surgical tool 400 and/or displaying detailed instructions for the user, as at 1110.

If the knife was commanded to retract, the computer system 606 may be programmed to verify if the knife was successfully retracted by the robotic surgical system, as at 1126. This may be done by checking the progress and signals provided by the torque sensors 628 and/or the rotary encoders 630. If the knife was not successfully retracted, then that may be an indication of user-activated bailout, and the method may proceed to disabling the surgical tool 400 and/or displaying detailed instructions for the user, as at 1110. However, if it is determined that the knife was successfully retracted, that may be an indication that the firing sequence of the end effector 404 is complete and the method 1100 may further include setting the bailout Boolean value to "false" in the computer system 606, as at 1228. Setting the bailout Boolean value to "false" in the computer system 606 indicates that the surgical tool 400 has not been bailed out, but instead indicates that the firing sequence was successfully completed under robotic control. At this point, the surgical tool 400 may be ready to fire again and thus the method 1100 may return to step 1108.

Figure 12:
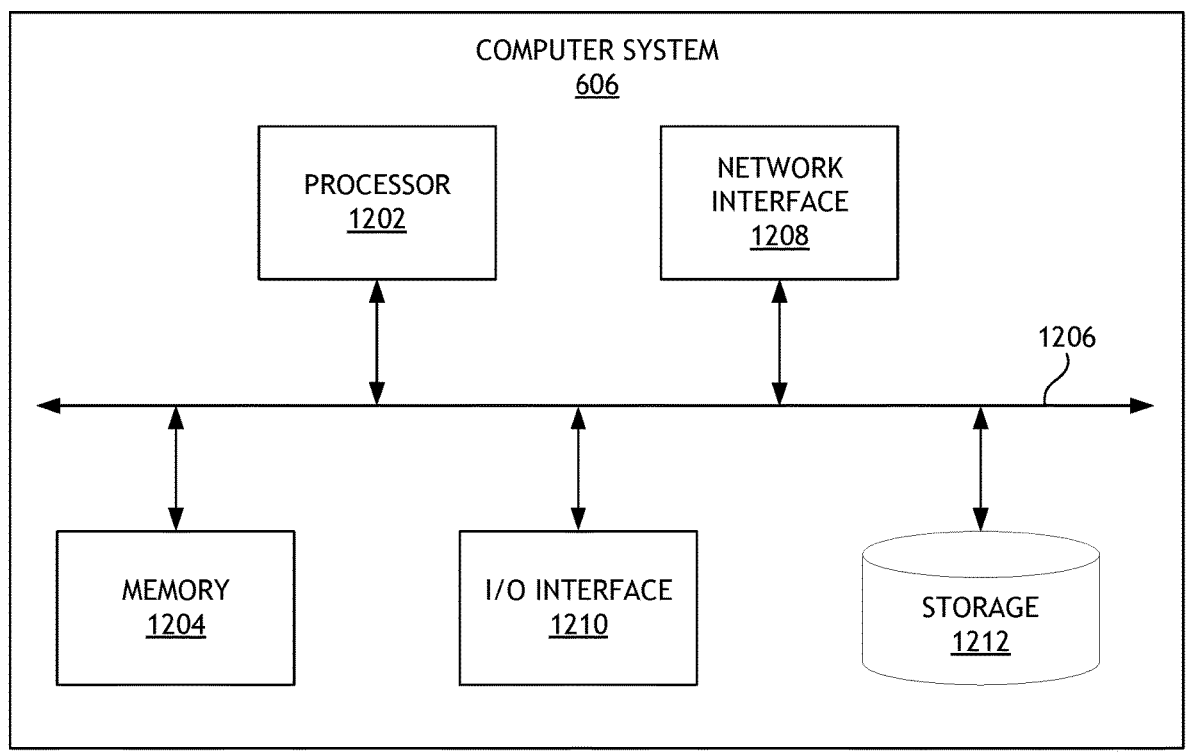
FIG. 12 illustrates an example embodiment of the computer system of FIG. 6.

FIG. 12 illustrates an example embodiment of the computer system 606. As shown, the computer system 606 includes one or more processors 1202, which can control the operation of the computer system 606. "Processors" are also referred to herein as "controllers." The processor(s) 1202 can include any type of microprocessor or central processing unit (CPU), including programmable general-purpose or special-purpose microprocessors and/or any one of a variety of proprietary or commercially available single or multi-processor systems. The computer system 606 can also include one or more memories 1204, which can provide temporary storage for code to be executed by the processor(s) 1202 or for data acquired from one or more users, storage devices, and/or databases. The memory 1204 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 606 can be coupled to a bus system 1206. The illustrated bus system 1206 is an abstraction that represents any one or more separate physical busses, communication lines/interfaces, and/or multi-drop or point-to-point connections, connected by appropriate bridges, adapters, and/or controllers. The computer system 606 can also include one or more network interface(s) 1208, one or more input/output (TO) interface(s) 1210, and one or more storage device(s) 1212.

The network interface(s) 1208 can enable the computer system 606 to communicate with remote devices, e.g., other computer systems, over a network, and can be, for non-limiting example, remote desktop connection interfaces, Ethernet adapters, and/or other local area network (LAN) adapters. The IO interface(s) 1210 can include one or more interface components to connect the computer system 606 with other electronic equipment. For non-limiting example, the IO interface(s) 1210 can include high speed data ports, such as universal serial bus (USB) ports, 1394 ports, Wi-Fi, Bluetooth, etc. Additionally, the computer system 606 can be accessible to a human user, and thus the IO interface(s) 1210 can include displays, speakers, keyboards, pointing devices, and/or various other video, audio, or alphanumeric interfaces. The storage device(s) 1212 can include any conventional medium for storing data in a non-volatile and/or non-transient manner. The storage device(s) 1212 can thus hold data and/or instructions in a persistent state, i.e., the value(s) are retained despite interruption of power to the computer system 606. The storage device(s) 1212 can include one or more hard disk drives, flash drives, USB drives, optical drives, various media cards, diskettes, compact discs, and/or any combination thereof and can be directly connected to the computer system 606 or remotely connected thereto, such as over a network. In an exemplary embodiment, the storage device(s) 1212 can include a tangible or non-transitory computer readable medium configured to store data, e.g., a hard disk drive, a flash drive, a USB drive, an optical drive, a media card, a diskette, a compact disc, etc.

The elements illustrated in FIG. 11 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 606 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP)

requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 606 can also include a web server for generating and/or delivering the web pages to client computer systems.

In an exemplary embodiment, the computer system 606 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

The computer system 606 can also include any of a variety of other software and/or hardware components, including by way of non-limiting example, operating systems and database management systems. Although an exemplary computer system is depicted and described herein, it will be appreciated that this is for the sake of generality and convenience. In other embodiments, the computer system may differ in architecture and operation from that shown and described here.

Embodiments disclosed herein include:

A. A method of operating a surgical tool having a drive housing, a shaft extending from the drive housing, and an end effector arranged at an end of the shaft, the method including sending a command signal from a computer system to a motor to drive rotation of a drive shaft mounted within the drive housing, monitoring one or more operational parameters of the motor with one or more monitoring devices in communication with the computer system, measuring an unexpected change in the one or more operational parameters of the motor with the one or more monitoring devices, wherein the unexpected change includes a measured operational parameter that is inconsistent with the command signal, reporting the unexpected change to the computer system as a bailout signal, and disabling the surgical tool once the bailout signal is received at the computer system.

B. A method of operating a surgical tool having a drive housing, a shaft extending from the drive housing, and an end effector arranged at an end of the shaft, the method including coupling the drive housing to a tool driver of a robotic surgical system, sending a command signal from a computer system to a motor of the tool driver to drive rotation of a drive shaft mounted within the drive housing and thereby firing the end effector, setting a bailout Boolean value to "true" in the computer system once the command signal is sent to fire the end effector, and setting the bailout Boolean value to "false" in the computer system once firing the end effector is completed.

Each of embodiments A and B may have one or more of the following additional elements in any combination: Element 1: wherein the one or more monitoring devices comprise at least one of a torque sensor and a rotary encoder, and wherein monitoring the one or more operational parameters of the motor comprises monitoring at least one of torque and rotational motion of the motor with the one or more monitoring devices. Element 2: wherein the unexpected change in the one or more operational parameters comprises at least one of a measured torque and a measured motion of the motor that is inconsistent with the command signal provided by the computer system to the motor. Element 3: wherein measuring the unexpected change in the one or more operational parameters is preceded by manually bailing out the surgical tool. Element 4: wherein manually bailing out the surgical tool comprises activating a manual knife bailout system of the surgical tool by operatively coupling a key to a transfer drive shaft mounted within the drive housing, the transfer drive shaft being interconnected by gearing to the drive shaft and a firing member, and the firing member being longitudinally movable within the drive housing and operatively coupled to a knife located at the end effector, and manually rotating the key in a first angular direction and thereby driving the firing member and the knife in a first longitudinal direction. Element 5: wherein the one or more operational parameters of the motor comprises at least one of torque and rotational motion of the motor, and wherein measuring the unexpected change in the one or more operational parameters comprises measuring at least one of the torque and the rotational motion of the motor as the key is manually rotated in the first direction. Element 6: wherein the key is operatively coupled to the transfer shaft at a bailout cap having one or more ramped surface features, the method further comprising manually rotating the key in a second angular direction opposite the first angular direction, and ratcheting the key over the one or more ramped surface features as the key is rotated in the second angular direction. Element 7: wherein manually bailing out the surgical tool comprises activating a manual jaw bailout system of the surgical tool by grasping a bailout tool arranged on an exterior of the drive housing and operatively coupled to a primary gear mounted within the drive housing, the primary gear being interconnected by gearing to the drive shaft and rotatably mounted to a closure yoke, wherein the closure yoke is coupled to a closure tube of the shaft and movable to actuate opposing jaws of the end effector, and manually rotating the bailout tool and thereby driving the closure yoke and the closure tube in a longitudinal direction to actuate the opposing jaws. Element 8: wherein the one or more operational parameters of the motor comprises at least one of torque and rotational motion of the motor, and wherein measuring the unexpected change in the one or more operational parameters comprises measuring at least one of the torque and the rotational motion of the motor as the bailout tool is manually rotated. Element 9: wherein disabling the surgical tool comprises rendering the surgical tool unavailable for future procedures. Element 10: wherein rendering the surgical tool unavailable for future procedures comprises at least one of allowing a knife located at the end effector to be retracted to a home position, preventing the knife from extending, permitting actuation of opposing jaws of the end effector, permitting articulation of a wrist interposing the end effector and the shaft, and permitting rotation of the shaft. Element 11: wherein disabling the surgical tool comprises communicating the bailout signal to an internal computer of the drive housing and storing the bailout signal in a memory of the internal computer. Element 12: wherein disabling the surgical tool comprises communicating the bailout signal to a central database.

Element 13: wherein firing the end effector comprises distally advancing a knife of the end effector relative to opposing jaws of the end effector, and retracting the knife to a home position. Element 14: further comprising manually bailing out the surgical tool before firing the end effector is completed, and disabling the surgical tool with the computer system based on the bailout Boolean value being "true" when the surgical tool is bailed out. Element 15: wherein disabling the surgical tool comprises at least one of rendering the surgical tool unavailable for future procedures and generating an alert that informs a user that the surgical tool was previously bailed out. Element 16: wherein the robotic surgical system is a first robotic surgical system, the method further comprising communicating the bailout Boolean value as "true" to an internal computer of the drive housing and storing the bailout Boolean value in a memory of the internal computer, manually bailing out the surgical tool before firing the end effector is completed, installing the surgical tool on a second robotic surgical system, querying the memory of the internal computer with the second robotic surgical system and recognizing the bailout Boolean value as "true", and initiating one or more remedial actions to ensure safe operation of the surgical tool on the second robotic surgical system. Element 17: wherein initiating the one or more remedial actions comprises disabling the surgical tool and thereby rendering the surgical tool unavailable for future procedures. Element 18: wherein initiating the one or more remedial actions comprises generating an alert that informs a user that the surgical tool was previously bailed out. Element 19: wherein generating the alert comprises displaying detailed instructions for the user on a visual display.

By way of non-limiting example, exemplary combinations applicable to A and B include: Element 1 with Element 2; Element 3 with Element 4; Element 4 with Element 5; Element 4 with Element 6; Element 3 with Element 7; Element 7 with Element 8; Element 9 with Element 10; Element 14 with Element 15; Element 16 with Element 17; Element 16 with Element 18; and Element 18 with Element 19.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
   a drive housing configured to be removably coupled to a tool driver of a robotic surgical system;
   a shaft extending from the drive housing;
   an end effector arranged at an end of the shaft; and
   a computer system including a memory and a processor operable to execute commands stored on the memory, the computer system being programmed to:
      send a command signal to a motor of the tool driver to drive rotation of a drive shaft mounted within the drive housing;
      monitor torque and rotational motion of the motor with a torque sensor and a rotary encoder, respectively, in communication with the computer system;
      measure an unexpected change in at least one of the torque and the rotational motion of the motor with at least one of the torque sensor and the rotary encoder when the surgical tool is manually bailed out by manually rotating the drive shaft and backdriving the motor;
      report the unexpected change as a bailout signal; and
      disable the surgical tool once the bailout signal is received.

2. The surgical tool of claim 1, wherein, by disabling the surgical tool, the computer system is further programmed to render the surgical tool unavailable for future procedures.

3. The surgical tool of claim 2, wherein rendering the surgical tool unavailable for future procedures comprises at least one of:
   allowing a knife located at the end effector to be retracted to a home position;
   preventing the knife from extending;
   permitting actuation of opposing jaws of the end effector;
   permitting articulation of a wrist interposing the end effector and the shaft; and
   permitting rotation of the shaft.

4. The surgical tool of claim 1, wherein, by disabling the surgical tool, the computer system is further programmed to:
   generate an alert perceivable by a user that the surgical tool has been bailed out; and
   override the alert and thereby allowing the user to proceed with operation of the surgical tool.

5. The surgical tool of claim 1, wherein the robotic surgical system is a first robotic surgical system and the surgical tool further includes an internal computer housed within the drive housing and including an internal computer memory, and wherein the computer system is further programmed to:
   communicate the bailout signal to the internal computer such that the bailout signal is stored in the internal computer memory;

upon installing the surgical tool on a tool driver of a second robotic surgical system, query the internal computer memory with the second robotic surgical system and determine that the surgical tool was previously bailed out; and initiate one or more remedial actions to ensure safe operation of the surgical tool on the second robotic surgical system.

6. The surgical tool of claim 5, wherein initiating the one or more remedial actions comprises disabling the surgical tool and thereby rendering the surgical tool unavailable for future procedures.

7. The surgical tool of claim 5, wherein initiating the one or more remedial actions comprises generating an alert that informs a user that the surgical tool was previously bailed out.

8. The surgical tool of claim 7, wherein generating the alert comprises displaying detailed instructions for the user on a visual display.

9. The surgical tool of claim 1, wherein the surgical tool is manually bailed out using a bailout mechanism that includes:

a key mounted within the drive housing; and a transfer drive shaft interconnected by gearing to the drive shaft and a firing member, the firing member being longitudinally movable within the drive housing and operatively coupled to a knife located at the end effector, wherein a user accesses the key and manually couples the key to the transfer drive shaft, and wherein manually rotating the key in a first angular direction drives the firing member and the knife in a first longitudinal direction.

10. The surgical tool of claim 9, wherein the key is operatively coupled to the transfer drive shaft at a bailout cap having one or more ramped surface features, and wherein manually rotating the key in a second angular direction opposite the first angular direction ratchets the key over the one or more ramped surface features as the key is rotated in the second angular direction.

11. The surgical tool of claim 1, wherein the surgical tool is manually bailed out using a bailout mechanism that includes:

a bailout tool arranged on an exterior of the drive housing and operatively coupled to a primary gear mounted within the drive housing, the primary gear being interconnected by gearing to the drive shaft and rotatably mounted to a closure yoke, wherein the closure yoke is coupled to a closure tube of the shaft and movable to actuate opposing jaws of the end effector, and wherein manually rotating the bailout tool drives the closure yoke and the closure tube in a longitudinal direction to actuate the opposing jaws.

12. The surgical tool of claim 1, wherein the computer system is further programmed to communicate the bailout signal to a central database to disable the surgical tool.

13. A surgical tool, comprising:

a drive housing configured to be removably coupled to a tool driver of a robotic surgical system;

a shaft extending from the drive housing;

an end effector arranged at an end of the shaft; and a computer system including a memory and a processor operable to execute commands stored on the memory, the computer system being programmed to:

send a command signal to a motor of the tool driver to drive rotation of a drive shaft mounted within the drive housing and thereby commence a firing sequence of the end effector;

set a bailout Boolean value to "true" in the computer system once the command signal is sent to commence the firing sequence;

set the bailout Boolean value to "false" in the computer system if the firing sequence is fully completed; and maintain the bailout Boolean value as "true" if the surgical tool is manually bailed out before completing the firing sequence.

14. The surgical tool of claim 13, wherein the firing sequence of the end effector comprises:

distally advancing a knife of the end effector relative to opposing jaws of the end effector; and retracting the knife to a home position.

15. The surgical tool of claim 13, wherein the computer system is further programmed to disable the surgical tool when the bailout Boolean value is "true" following the surgical tool being manually bailed out.

16. The surgical tool of claim 15, wherein, by disabling the surgical tool, the computer system is further programmed to at least one of render the surgical tool unavailable for future procedures or generate an alert that informs a user that the surgical tool was previously bailed out.

17. The surgical tool of claim 13, wherein the robotic surgical system is a first robotic surgical system and the surgical tool further includes an internal computer housed within the drive housing and including an internal computer memory, and wherein the computer system is further programmed to:

communicate the bailout Boolean value as "true" to the internal computer and store the bailout Boolean value in the internal computer memory;

upon manually bailing out the surgical tool before completing the firing sequence and subsequently installing the surgical tool on a tool driver of a second robotic surgical system, query the internal computer memory with the second robotic surgical system and determine that the surgical tool was previously bailed out; and initiate one or more remedial actions to ensure safe operation of the surgical tool on the second robotic surgical system.

18. The surgical tool of claim 17, wherein the one or more remedial actions include disabling the surgical tool and thereby rendering the surgical tool unavailable for future procedures.

19. The surgical tool of claim 17, wherein the one or more remedial actions include generating an alert that informs a user that the surgical tool was previously bailed out.

20. The surgical tool of claim 19, wherein the alert includes detailed instructions displayed for the user on a visual display.

* * * * *